United States Patent
Iwema Bakker et al.

(10) Patent No.: US 9,227,960 B2
(45) Date of Patent: Jan. 5, 2016

(54) BISARYL (THIO)MORPHOLINE DERIVATIVES AS S1P MODULATORS

(71) Applicant: ABBVIE B.V., Hoofddorp (NL)

(72) Inventors: Wouter I. Iwema Bakker, Hoofddorp (NL); Raymond Bronger, Hoofddorp (NL)

(73) Assignee: ABBVIE B.V., Hoofddorp (NL)

( * ) Notice: Subject to any disclaimer, the term of this patent is extended or adjusted under 35 U.S.C. 154(b) by 0 days.

(21) Appl. No.: 14/666,089

(22) Filed: Mar. 23, 2015

(65) Prior Publication Data
US 2015/0191457 A1 Jul. 9, 2015

Related U.S. Application Data

(62) Division of application No. 13/808,900, filed as application No. PCT/EP2011/061590 on Jul. 8, 2011, now Pat. No. 9,029,371.

(60) Provisional application No. 61/452,977, filed on Mar. 15, 2011, provisional application No. 61/362,785, filed on Jul. 9, 2010.

(30) Foreign Application Priority Data

Jul. 9, 2010 (EP) .................................... 10169108
Mar. 15, 2011 (EP) .................................... 11158269

(51) Int. Cl.
*C07D 413/10* (2006.01)
*C07D 265/30* (2006.01)
*C07D 295/15* (2006.01)

(52) U.S. Cl.
CPC ............ *C07D 413/10* (2013.01); *C07D 265/30* (2013.01); *C07D 295/15* (2013.01)

(58) Field of Classification Search
CPC .................................................... C07D 295/15

USPC .................. 544/58.1, 58.2, 59, 60; 514/227.5, 514/227.8
See application file for complete search history.

(56) References Cited

FOREIGN PATENT DOCUMENTS

| WO | 2008/129029 | 10/2008 |
|---|---|---|
| WO | 2011023795 | 3/2011 |
| WO | 2011095579 | 8/2011 |

OTHER PUBLICATIONS

International Search Report and Written Opinion for Application No. PCT/EP2011/061590 dated Aug. 12, 2011 (7 pages).
Hu A-X et al., "Synthesis and Cyclooxygenase-2 Inhibitory Activity of 2-(2-arylmorpholino)ethyl Ester of Naproxen," ACTA Chimica Sinca, vol. 66, 2008, pp. 2553-2257.

*Primary Examiner* — Kahsay Habte
(74) *Attorney, Agent, or Firm* — Lisa V. Mueller; Michael Best & Friedrich LLP

(57) ABSTRACT

Described are compounds that are modulators of the S1P receptors, and pharmaceutical compositions comprising the compounds. Also described are methods of using the compounds and compositions for treating, alleviating, or preventing S1P receptor mediated diseases and conditions.

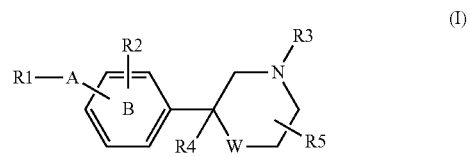

13 Claims, No Drawings

BISARYL (THIO)MORPHOLINE DERIVATIVES AS S1P MODULATORS

CROSS-REFERENCE TO RELATED APPLICATIONS

This is a divisional of U.S. patent application Ser. No. 13/808,900, filed on Apr. 18, 2013, now U.S. Pat. No. 9,029,371, which is a U.S. national stage entry of International Patent Application No. PCT/EP2011/061590, filed on Jul. 8, 2011, which claims priority to U.S. Provisional Patent Application No. 61/452,977, filed on Mar. 15, 2011, U.S. Provisional Patent Application No. 61/362,785, filed on Jul. 9, 2010, European Patent Application No. 11158269.8, filed on Mar. 15, 2011, and European Patent Application No. 10169108.7, filed on Jul. 9, 2010, the entire contents of all of which are fully incorporated herein by reference.

FIELD OF THE INVENTION

This invention relates to new bisaryl(thio)morpholine derivatives having affinity to S1P receptors, a pharmaceutical composition containing said compounds, as well as the use of said compounds for the preparation of a medicament for treating, alleviating or preventing diseases and conditions in which any S1P receptor is involved or in which modulation of the endogenous S1P signaling system via any S1P receptor is involved.

BACKGROUND OF THE INVENTION

Sphingosine-1-phosphate (S1P) is a bioactive sphingolipid that mediates a wide variety of cellular responses, such as proliferation, cytoskeletal organization and migration, adherence- and tight junction assembly, and morphogenesis. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and S1P5 (EDG-8). S1P can produce cytoskeletal re-arrangements in many cell types to regulate immune cell trafficking, vascular homeostasis and cell communication in the central nervous system (CNS) and in peripheral organ systems.

It is known that S1P is secreted by vascular endothelium and is present in blood at concentrations of 200-900 nanomolar and is bound by albumin and other plasma proteins. This provides both a stable reservoir in extracellular fluids and efficient delivery to high-affinity cell-surface receptors. S1P binds with low nanomolar affinity to the five receptors S1P1-5. In addition, platelets also contain S1P and may be locally released to cause e.g. vasoconstriction. The receptor subtypes S1P1, S1P2 and S1P3 are widely expressed and represent dominant receptors in the cardiovascular system. Further, S1P1 is also a receptor on lymphocytes. S1P4 receptors are almost exclusively in the haematopoietic and lymphoid system. S1P5 is primarily (though not exclusively) expressed in central nervous system. The expression of S1P5 appears to be restricted to oligodendrocytes in mice, the myelinating cells of the brain, while in rat and man expression at the level of astrocytes and endothelial cells was found but not on oligodendrocytes.

S1P receptor modulators are compounds which signal as (ant)agonists at one or more S1P receptors. The present invention relates to modulators of the S1P5 receptor, in particular agonists, and preferably to agonists with selectivity over S1P1 and/or S1P3 receptors, in view of unwanted cardiovascular and/or immunomodulatory effects. It has now been found that S1P5 agonists can be used in the treatment of cognitive disorders, in particular age-related cognitive decline.

Although research is ongoing to develop therapeutics that can be used to treat age related cognitive decline and dementia, this has not yet resulted in many successful candidates. Therefore, there is a need for new therapeutics with the desired properties.

DESCRIPTION OF THE INVENTION

It has now been found that bisaryl(thio)morpholine derivatives of the formula (I)

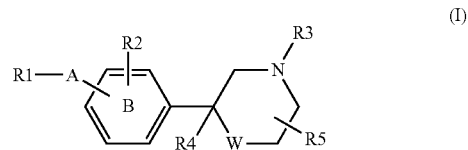

wherein
R1 is an aryl substitutent selected from phenyl, pyridyl, pyrimidinyl, biphenyl and naphthyl, each optionally substituted with one or more substituents independently selected from halogen, (1-6C)alkyl optionally substituted with one or more fluoro atoms, (1-4C)alkoxy optionally substituted with one or more fluoro atoms, amino, di(1-4C)alkylamino, —SO$_2$-(1-4C)alkyl, —CO-(1-4C)alkyl, —CO—O-(1-4C)alkyl and —NH—CO-(1-4C)alkyl, or substituted with phenoxy, benzyl, benzyloxy, phenylethyl or morpholinyl, each optionally substituted with (1-4C)alkyl, and (8-10C)bicyclic group, bicyclic heterocycle, each optionally substituted with (1-4C)alkyl optionally substituted with one or more fluoro atoms or oxo;
A is selected from —CO—, —NH—, —O—, —S—, —SO— or —SO$_2$—;
ring structure B optionally contains one nitrogen atom;
R2 is H, (1-4C)alkyl optionally substituted with one or more fluoro atoms, (1-4C)alkoxy optionally substituted with one or more fluoro atoms, or halogen; and
R3 is (1-4C)alkylene-R6 wherein the alkylene group may be substituted with (CH$_2$)$_2$ to form a cyclopropyl moiety or with one or more halogen atoms, or R3 is (3-6C)cycloalkylene-R5 or —CO—CH$_2$—R6, wherein R6 is —OH, —PO$_3$H$_2$, —OPO$_3$H$_2$, —COOH, —COO(1-4C)alkyl or tetrazol-5-yl;
R4 is H or (1-4C)alkyl;
R5 is one or more substituents independently selected from H, (1-4C)alkyl or oxo;
W is —O—, —S—, —SO— or —SO$_2$—;
or a pharmaceutically acceptable salt, a solvate or hydrate thereof, with the proviso that the derivative of formula (I) is not 2-[4-(4-chlorophenoxy)-2-chloro-phenyl]-4-morpholineethanol, display affinity for Slip receptors. In particular, compounds of the invention show selective affinity for the S1P5 receptor over the S1P1 and/or S1P3 receptor(s).

The use of the compound 2-[4-(4-chlorophenoxy)-2-chloro-phenyl]-4-morpholineethanol as a reagent in the production of 2-(2-arylmorpholino)ethyl esters of naproxen is described in Acta Chimica Sinica, vol. 66 (No. 22), 2008, 2553-2557, Hu, Ai-Xi et al, XP009137465. No pharmacological activity of the compound is reported.

The compounds of the invention are modulators of the S1P receptor, in particular of the S1P5 receptor. More specifically, the compounds of the invention are S1P5 receptor agonists. The compounds of the invention are useful for treating, alleviating and preventing diseases and conditions in which (any) S1P receptor(s)—in particular S1P5—is (are) involved or in which modulation of the endogenous S1P signaling system via any S1P receptor is involved. In particular, the compounds of the present invention may be used to treat, alleviate or prevent CNS (central nervous system) disorders, such as neurodegenerative disorders, in particular—but not limited to—cognitive disorders (in particular age-related cognitive decline) and related conditions, Alzheimer's disease, (vascular) dementia, Nieman's Pick disease, and cognitive deficits in schizophrenia, obsessive-compulsive behavior, major depression and autism, multiple sclerosis, pain, etc. Preferably, the compounds of the present invention may be used to treat, alleviate or prevent cognitive disorders (in particular age-related cognitive decline) and related conditions.

In an embodiment of the invention, the compounds have formula (I) wherein R3 is selected from —(CH$_2$)$_2$—OH, —CH$_2$—COOH, —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH, —CH$_2$—CF$_2$—COOH, —CO—CH$_2$—COOH, —(CH$_2$)$_2$—PO$_3$H$_2$, —(CH$_2$)$_3$—PO$_3$H$_2$, —(CH$_2$)$_2$—OPO$_3$H$_2$, —(CH$_2$)$_3$—OPO$_3$H$_2$, —CH$_2$-tetrazol-5-yl, —(CH$_2$)$_2$-tetrazol-5-yl and —(CH$_2$)$_3$-tetrazol-5-yl. Preferred R3 groups are selected from —CH$_2$—COOH, —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH, —(CH$_2$)$_2$—PO$_3$H$_2$, —(CH$_2$)$_3$—PO$_3$H$_2$ and —(CH$_2$)$_2$—OPO$_3$H$_2$ and in particular —(CH$_2$)$_2$—COOH and —(CH$_2$)$_2$—PO$_3$H$_2$. In particular preferred R3 groups are selected from —CH$_2$—COOH, —(CH$_2$)$_2$—COOH, —(CH$_2$)$_3$—COOH, —CH$_2$—CHCH$_3$—COOH, —CH$_2$—C(CH$_3$)$_2$—COOH and —CHCH$_3$—CH$_2$—COOH. Most preferred is —(CH$_2$)$_2$—COOH.

In another embodiment of the invention, the compounds have the structure (II)

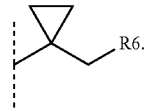

(II)

In preferred embodiments of the invention the ring structure B is phenylene.

In a further embodiment of the invention, R4 is methyl or H. Preferably, R4 is H.

In another embodiment, the compounds have formula (I) wherein R2 is H or halogen. In further embodiments, R2 is trifluoromethyl.

Further, in an embodiment of the invention, A is —CO—, —NH— or —O—.

In further embodiments of the invention, R1 is selected from pyridyl, pyrimidinyl, biphenyl, naphthyl, dihydrobenzofuranyl optionally substituted with oxo, benzdioxanyl, quinolinyl, isoquinolinyl and from phenyl optionally substituted with one or more substituents independently selected from halogen, (1-6C)alkyl, di(1-4C)alkylamino (preferably dimethylamino), —SO$_2$-(1-4C)alkyl, —CO-(1-4C)alkyl, —CO—O-(1-4C)alkyl, —NH—CO-(1-4C)alkyl, difluoromethyl, trifluoromethyl, difluoromethoxy and trifluoromethoxy, or substituted with phenoxy, benzyl, benzyloxy, phenylethyl or morpholinyl. In preferred embodiments, R1 is selected from phenyl substituted with one, two or three halogens, phenyl substituted with one halogen and one methyl or trifluoromethyl, phenyl substituted with one or two methyl groups, phenyl substituted with one or two trifluoromethyl groups, phenyl substituted with either one methoxy, one trifluoromethoxy, one —CO-methyl, one —SO$_2$-methyl, one —NH—CO-methyl or one —CO—O-methyl.

In preferred embodiments, W is —O— or —S—.

In embodiments of the invention, R5 is H or represents an oxo group or two methyl groups, which methyl groups are preferably attached to the same carbon atom in the (thio) morpholine moiety.

The term halogen refers to fluoro, chloro, bromo, or iodo. Preferred halogens are fluoro and chloro, and in particular chloro.

The term (1-6C)alkyl or (1-4C)alkyl means a branched or unbranched alkyl group having 1-6 or 1-4 carbon atoms, respectively, for example methyl, ethyl, propyl, isopropyl and butyl. A preferred alkyl group is methyl.

The term (1-4C)alkoxy means an alkoxy group having 1-4 carbon atoms, wherein the alkyl moiety is as defined above.

The term (1-4C)alkylene means a branched or unbranched alkylene group having 1-4 carbon atoms, for example methylene, —CCH$_3$CH$_2$—, and the like. In the definition of R3 which is (1-4C)alkylene-R6, one or more carbon atoms in the alkylene group may (amongst others) independently be substituted with (CH$_2$)$_2$ to form a cyclopropyl moiety, meaning to form a R3 group such as

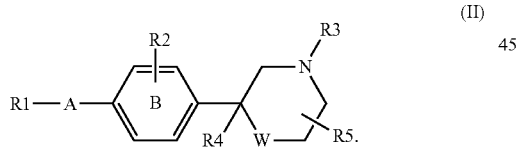

The term (3-6C)cycloalkylene means a cyclic alkyl group having two attachment points. Preferred is 1,3-cyclobutylene, having the structure

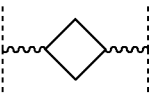

The term (8-10C)bicyclic group means a fused ring system of an aromatic and a non-aromatic ring structure having together 8-10 carbon atoms, for example the indane group.

The term bicyclic heterocycle encompasses bicyclic heteroaryl groups, for example indolyl, indazolyl, isoindolyl, indolizinyl, benzimidazolyl, imidazothiazolyl, imidazopyridinyl, benzfuranyl, dihydrobenzofuranyl, benzdioxanyl, quinolinyl, isoquinolinyl, quinolizinyl, tetrahydroisoquinolinyl, and the like. Preferred bicyclic heterocycles are dihydrobenzofuranyl, benzdioxanyl, quinolinyl and isoquinolinyl.

With reference to substituents, the term "independently" means that the substituents may be the same or different from each other in the same molecule.

The compounds of the invention may suitably be prepared by methods available in the art, and as illustrated in the experimental section of this description.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds may exist as polymorphs and as such are intended to be included in the present invention. In addition, compounds may form solvates with water (i.e., hydrates) or common organic solvents, and such solvates are also intended to be encompassed within the scope of this invention.

Isotopically-labeled compound of formula (I) or pharmaceutically acceptable salts thereof, including compounds of formula (I) isotopically-labeled to be detectable by PET or SPECT, also fall within the scope of the invention. The same applies to compounds of formula (I) labeled with $[^{13}C]$-, $[^{14}C]$-, $[^{3}H]$-, $[^{18}F]$-, $[^{125}I]$- or other isotopically enriched atoms, suitable for receptor binding or metabolism studies.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when isolating and purifying the compounds of the invention, or separately by reacting them with pharmaceutically acceptable non-toxic bases or acids, including inorganic or organic bases and inorganic or organic acids.

The compounds of the invention may be administered enterally or parenterally. The exact dose and regimen of these compounds and compositions thereof will be dependent on the biological activity of the compound per se, the age, weight and sex of the patient, the needs of the individual subject to whom the medicament is administered, the degree of affliction or need and the judgment of the medical practitioner. In general, parenteral administration requires lower dosages than other methods of administration which are more dependent upon adsorption. However, the dosages for humans are preferably 0.001-10 mg per kg body weight. In general, enteral and parenteral dosages will be in the range of 0.1 to 1,000 mg per day of total active ingredients.

Mixed with pharmaceutically suitable auxiliaries, e.g. as described in the standard reference "Remington, The Science and Practice of Pharmacy" (21$^{st}$ edition, Lippincott Williams & Wilkins, 2005, see especially Part 5: Pharmaceutical Manufacturing) the compounds may be compressed into solid dosage units, such as pills or tablets, or be processed into capsules or suppositories. By means of pharmaceutically suitable liquids the compounds can also be applied in the form of a solution, suspension or emulsion.

For making dosage units, e.g. tablets, the use of conventional additives such as fillers, colorants, polymeric binders and the like, is contemplated. In general, any pharmaceutically suitable additive which does not interfere with the function of the active compounds can be used.

Suitable carriers with which the compounds of the invention can be administered include for instance lactose, starch, cellulose derivatives and the like, or mixtures thereof, used in suitable amounts. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

Pharmaceutical compositions of the invention may be formulated for any route of administration and comprise at least one compound of the present invention and pharmaceutically acceptable salts thereof, with any pharmaceutically suitable ingredient, excipient, carrier, adjuvant or vehicle.

By "pharmaceutically suitable" it is meant that the carrier, diluent or excipient must be compatible with the other ingredients of the formulation and not deleterious to the recipient thereof.

In an embodiment of the invention, a pharmaceutical pack or kit is provided comprising one or more containers filled with one or more pharmaceutical compositions of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document.

The following examples are intended to further illustrate the invention in more detail.

Any novel intermediate as disclosed herein is a further embodiment of the present invention.

Examples

§1. Materials and Methods

Nuclear magnetic resonance spectra ($^{1}$H NMR) were determined in the indicated solvent using a Bruker Avance-I 400 with a 9.4 T magnet ($^{1}$H: 400 MHz, $^{13}$C: 100 MHz), equipped with a BBI inversie broadband probehead with Z-gradient and ATM, or a Bruker Avance-DRX 600 with a 14.1 T magnet, equipped with a TXI inverse triple resonance cryoprobehead with Z-gradient and ATM, at 300 K, unless indicated otherwise. The spectra were determined in deuterated chloroform (CDCl$_3$) with 99.8 atom % D; or in dimethylsulfoxide-d$_6$ (DMSO-d$_6$) containing 0.03 v/v % tetramethylsilane; both obtained from Aldrich Chemical shifts (δ) are given in ppm downfield from tetramethylsilane. Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of D₂O.

Melting points were recorded on a Buchi B-545 melting point apparatus.

All reactions involving moisture sensitive compounds or conditions were carried out under an anhydrous nitrogen atmosphere.

Reactions were monitored by using thin-layer chromatography (TLC) on silica coated plastic sheets (Merck precoated silica gel 60 F254) with the indicated eluent. Spots were visualised by UV light (254 nm) or I₂.

Liquid Chromatography-Mass Spectrometry (LC-MS)

Column: Waters Sunfire C18, 30×4.6 mm with 2.5 □m particles. The column is thermo stated in a column oven at 23° C.

Detection: UV/VIS meter with the wavelength set to 254 nm+evaporative light scattering detector operating at 70° Celsius and 1.7 bar N₂ pressure.

| steptotal | time (min) | flow (ul/min) | A (%) | B (%) |
|---|---|---|---|---|
| 0 | 0 | 1800 | 95 | 5 |
| 1 | 1.8 | 1800 | 0 | 100 |
| 2 | 2.5 | 1800 | 0 | 100 |
| 3 | 2.7 | 1800 | 95 | 5 |

A = 99.8% Water with 0.2% HCOOH
B = 99.8% CH₃CN with 0.2% HCOOH

The reported retention times ($R_t$) are for the peak in the Total Ion Current (TIC) chromatogram which showed the mass for [M+H]+ within 0.5 amu accuracy of the calculated exact MW and had an associated peak in the Evaporative Light Scattering (ELS) chromatogram with a relative area % (purity) of >85%.

§2. General Aspects of Syntheses

Suitable syntheses of claimed compounds and intermediates containing 2-aryl-morpholine moieties follow routes as described below; see Scheme 1.

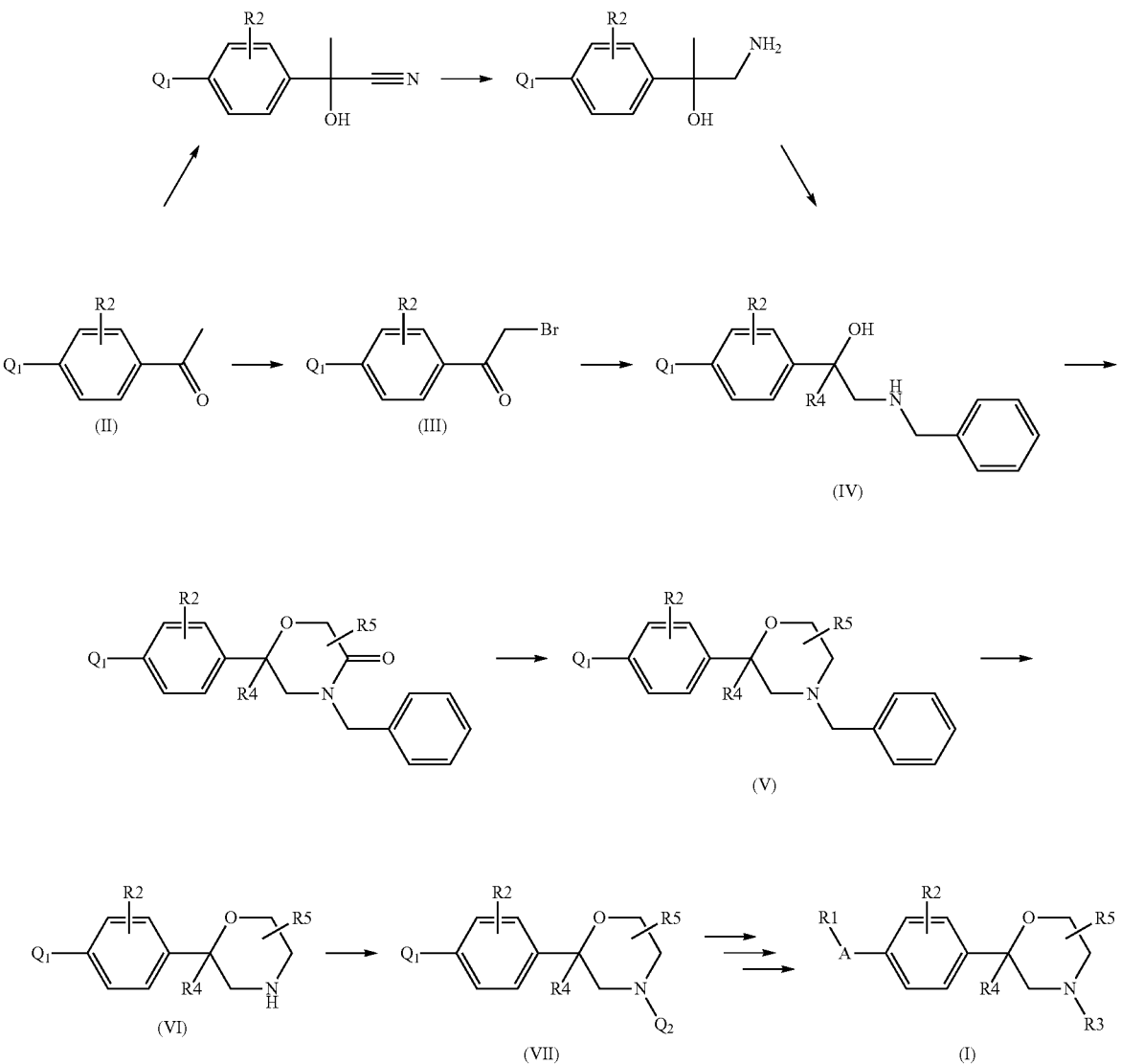

$Q_1$ is a group equal to R1-A, or a group that can be converted to R1-A. $Q_2$ is a group equal to R3, or a group that can be converted to R3. For details, see the full details given below.

The synthesis begins with a suitably substituted acetophenone (II). Suitably substituted acetophenones are commercially available or can be obtained from other commercially available acetophenones. For example by O-alkylation of (un)substituted 4-hydroxyacetophenones. This O-alkylation can be done with a suitable alkylating agent like 1-bromooctane or benzyl bromide, in solvents such as dimethylsulfoxide (DMSO), acetone, or acetonitrile, in the presence of a base like potassium hydroxide or potassium carbonate, at temperatures between 0° C. and 60° C.

as toluene, and finally reduction of the intermediate imine with sodium borohydride, in a solvent like methanol, at temperatures between −15° C. and room temperature.

The amino alcohols (IV) can be reacted with an activated chloroacetic acid or bromoacetic acid in a solvent such as dichloromethane with a base such as triethylamine, and subsequently cyclized in a solvent, such as 2-propanol or 2-methyl-2-butanol, with a base, such as potassium hydroxide or potassium tert-butoxide, to afford morpholin-3-ones. Those morpholin-3-ones can then be reduced with a reducing agent, such as borane or lithium aluminum hydride, in a solvent such as tetrahydrofuran, at temperatures between 0° C. and room temperature, to afford the N-benzyl morpholines (V). Some of the N-benzyl morpholines (V) can be converted to other N-benzyl morpholines (V), see Scheme 2.

Scheme 2

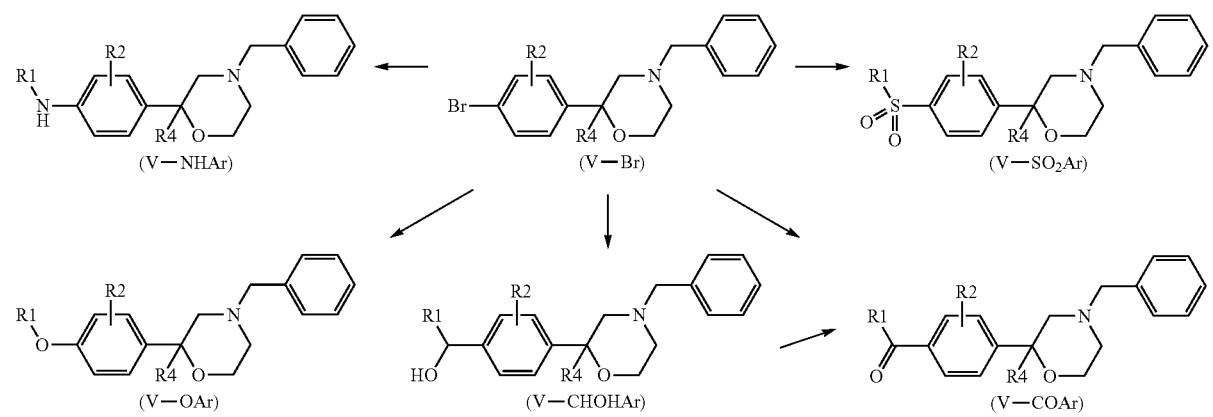

The suitably substituted acetophenone (II) is brominated to afford 2'-bromo-acetophenones (III). Bromination can be done with copper(II) bromide in a suitable solvent like ethyl acetate with heating under reflux; via reaction of the corresponding silyl enol ether, prepared with DIPEA and TMSOTf, at 0° C., with NBS in a solvent like dichloromethane, at room temperature; or with tetra-N-butylammonium tribromide, in a solvent like methanol, at room temperature.

Reaction of the 2'-bromoacetophenones with benzyl amine, in a solvent like ethanol and chloroform, at temperatures between 0° C. and room temperature, afforded aminoketones (R4=H) which where directly reduced with a reducing agent like sodium borohydride in a solvent like ethanol and chloroform, at temperatures between 0° C. and room temperature, to afford amino alcohols (IV, R4=H). Alternatively, 2'-bromoacetophenones (III) can be reduced with a suitable reducing agent like $NaBH_4$, in a solvent such as 1,4-dioxane, at room temperature, followed by treatment with a base, such as KOH, in a mixture of water and a suitable solvent, such as $Et_2O$, to afford 2-aryloxiranes, which on treatment with benzyl amine at a temperature of 80° C., afford amino alcohols (IV, R4=H). Another method for the synthesis of aminoalcohols (IV, R4=Me) is by the reaction of a suitably substituted acetophenone with trimethylsilyl cyanide in the presence of a lewis acid, like zinc iodide, at room temperature, in the neat. Followed by reduction of the intermediate cyanohydrin with a reducing agent, like lithium aluminum hydride, in a solvent like tetrahydrofuran, and subsequent imine formation with benzaldehyde in the presence of an acidic catalyst, like p-toluenesulfonic acid, in a solvent such For example V-Br can be coupled with a suitable aniline, under palladium catalysis in the presence of a base, like NaOtBu, in a solvent like toluene at temperatures around 100° C., to afford diarylamines V-NHAr. Compound V-Br can also be coupled with a suitable phenol, under copper(I) catalysis in the presence of a base, like cesium carbonate or sodium hydride, in a solvent such as toluene at temperatures around 110° C., to afford diarylethers V-OAr. Furthermore compounds V-Br can be reacted with n-butyl lithium is a solvent such as THF, to afford the corresponding lithium-compounds after bromine-lithium exchange. Those lithium compounds can then be reacted with a suitable eectrophile, such as a suitable benzaldehyde, a suitable benzenesulfonyl fluoride, or a suitable acylating reagent, to afford diarylmethanols (V-CHOHAr), diarylsulfones (V-$SO_2$Ar), or diarylketones (V-COAr). The diarylketones can also be obtained by oxidation of the diarylmethanols, with oxalyl chloride, DMSO and $Et_3N$ in a solventr such as $CH_2Cl_2$ at a temperature of −78° C. (Sworn-oxidation) (Scheme 2).

Removal of the N-benzyl group in the N-benzyl morpholines (V), can be done by reaction with ACE-Cl in a solvent such as 1,2-dichloroethane, followed by reaction of the intermediate carbamate with methanol, or alternatively, by hydrogenation in a solvent such as ethanol and a catalyst like palladium hydroxide to afford compounds VI. If compounds V contain a benzyloxy group (Q1=BnO), the benzyl-group is removed as well during the latter hydrogenation to afford compounds (VI—OH) (Scheme 1).

Morpholines (VI) can be reacted with an (meth)acrylic acid ester, in a so called Michael-addition, in a solvent such as acetonitrile, methanol, or N,N-dimethylformamide, at temperatures between room temperature and 85° C., and eventually with the addition of some base like triethylamine or 1,8-diazabicyclo[5.4.0]undec-7-ene, to afford morpholin-4-yl-propionic acid esters (VIIa, Q2=CH2CH2COOR') (Scheme 3). In case those morpholin-4-yl-propionic acid esters (VIIa, Q2=CH2CH2COOR') contain a phenolic group (VIIa-OH), those compounds can be coupled with a suitable arylbromide, under copper(I) catalysis in the presence of a base, like cesium carbonate or sodium hydride, in a solvent such as toluene at temperatures around 140° C., in a sealed vial, to afford diarylethers VIIa-OAr.

-continued

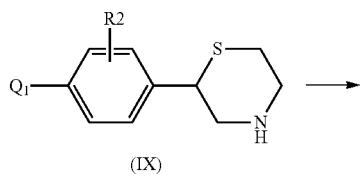

(IX)

Scheme 3

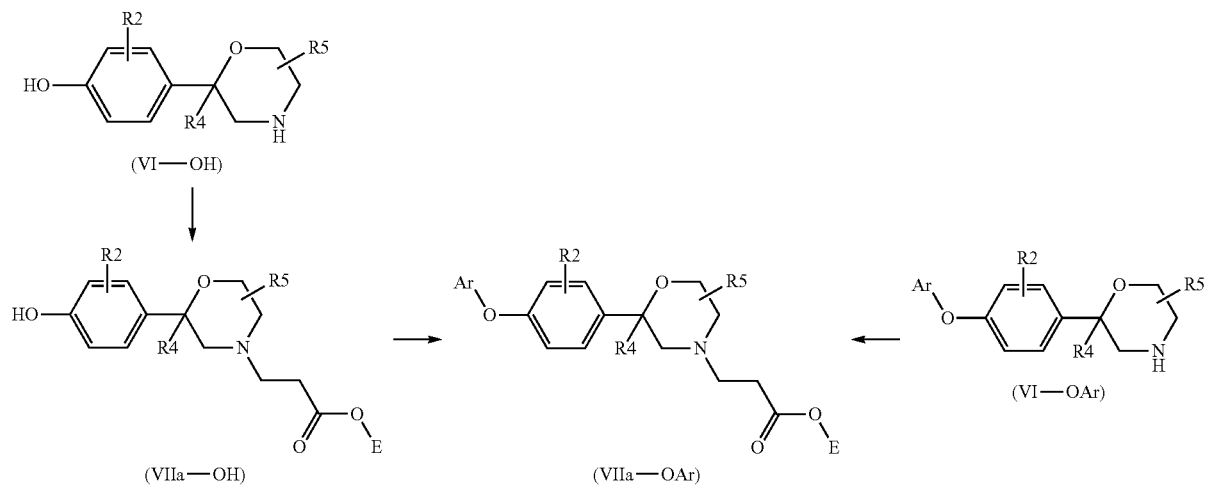

Compounds VIIa-OAr in which Ar=2,6-dichlorophenyl can be obtained from VIIa-OH by reaction with 2,6-dichlorofluorobenzene and $K_2CO_3$ in a solvent such as DMF, at temperatures around 100° C.

Compounds of type VII can be converted into the final compounds I by basic or acidic hydrolysis of the ester, depending on the nature of group E. As an example, tert-butyl esters (E=C(CH$_3$)$_3$) can be treated with an acid, such as trifluoroacetic acid or hydrogen chloride, in a solvent such as $CH_2Cl_2$ or 1,4-dioxane, at room temperature.

Compounds wherein W is —S—, —SO— or —SO$_2$— may be prepared as described below and shown in scheme 4.

-continued

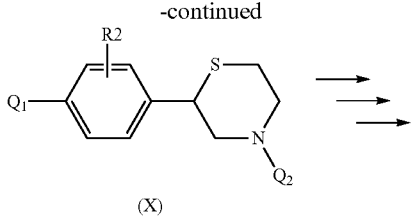

Scheme 4

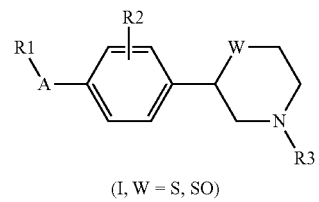

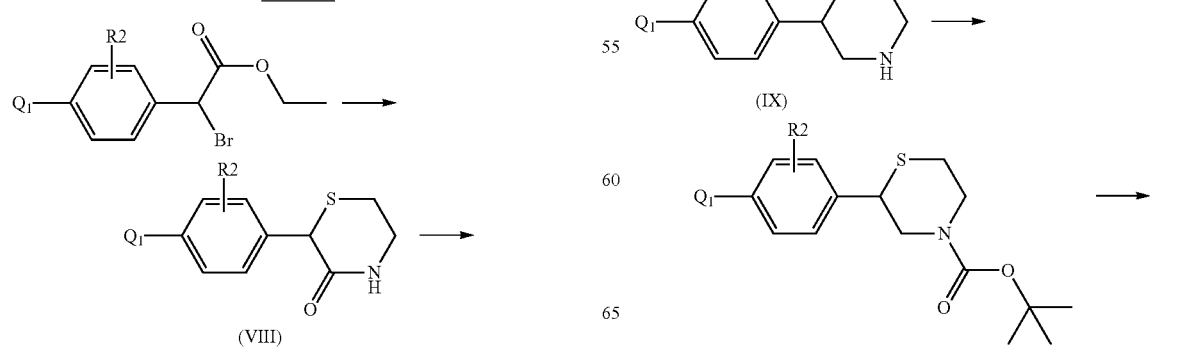

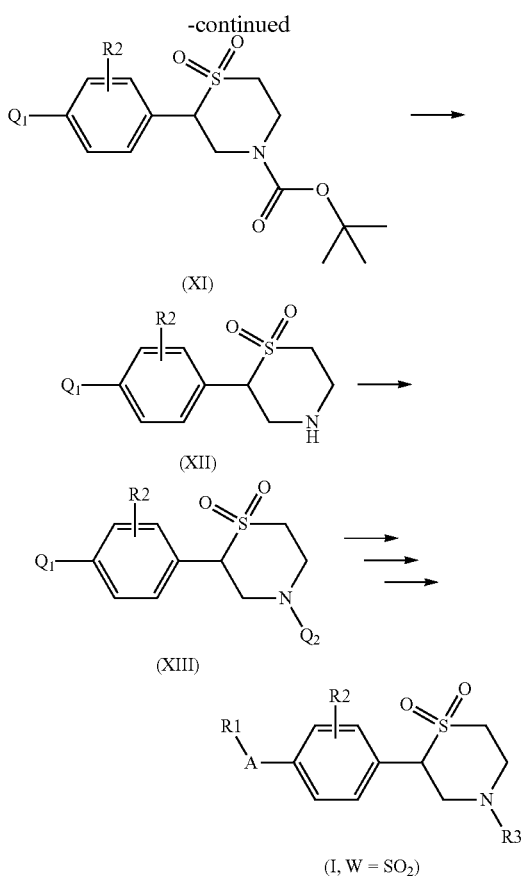

(XI)

(XII)

(XIII)

(I, W = SO₂)

Q₁ is a group equal to R1-A, or a group that can be converted to R1-A. Q₂ is a group equal to R3, or a group that can be converted to R3. For details, see the full details given below.

The synthesis begins with a suitably substituted bromophenyl-acetic acid ester. Suitably substituted bromo-phenyl-acetic acid esters are commercially available or can be obtained according to methods known in the literature. The bromo-phenyl-acetic acid ester is reacted with 2-aminoethanethiol, in the presence of a base, such as potassium carbonate, in a solvent such as ethanol, at room temperature, to obtain 2-aryl-thiomorpholin-3-ones (VIII). Those thiomorpholin-3-ones can then be reduced with a reducing agent such as borane in a solvent such as tetrahydrofuran, at temperatures between 0° C. and room temperature, to afford the 2-aryl-thiomorpholines (IX). Thiomorpholines (IX) can be reacted with an (meth)acrylic acid ester, in a so called Michael-addition, in a solvent such as acetonitrile, methanol, or N,N-dimethylformamide, at temperatures between room temperature and 85° C., and eventually with the addition of some base like triethylamine or 1,8-diazabicyclo[5.4.0]undec-7-ene, to afford morpholin-4-yl-propionic acid esters (X, Q2=CH2CH2COOR'). In case those thiomorpholin-4-yl-propionic acid esters (X, Q2=CH2CH2COOR') are substituted with bromine (X, Q1=Br), the bromine can be replaced by iodine (X, Q1=I) in a reaction with sodium iodide, catalysed by copper(I) iodide, in the presence of N,N-dimethylethylenediamine, in a solvent such as 1,4-dioxane, at temperatures around 130° C., in a closed vessel. Subsequently, the iodine (X, Q1=I), can be substituted by a suitable phenol, in the presence of a base such as potassium phosphate tribasic, and catalyzed by copper(I) iodide and picolinic acid, in a solvent such as dimethylsulfoxide, at a temperature around 90° C., to obtain compounds in which Q1 is equal to R1-A, and Q2=CH2CH2COOR'. In case R' is tert-butyl, the ester can be hydrolyzed with acid, such as hydrochloric acid, in a solvent such as 1,4-dioxane, at temperatures between room temperature and 80° C., to afford compounds (I, W=S). Thiomorpholines (X, W=S, Q1=R1-A, Q2=CH2CH2COOR'), can be oxidized with an oxidizing reagent such as potassium peroxymonosulfate (Oxone®), in a solvent such as methanol/water, at temperatures between 0° C. and room temperature to afford the thiomorpholine 1-oxides (X, W=SO, Q1=R1-A, Q2=CH2CH2COOR'). In case R' is tert-butyl acid hydrolysis as described for the thiomorpholines affords compounds (I, W=SO).

Thiomorpholines (IX) can be protected at the nitrogen with a suitable protecting group (P. G. M. Wuts, T. W. Greene Protective groups in organic synthesis, 4th ed., John Wiley & Sons, 2006), such as tert-butyloxycarbonyl (BOC), by reaction with di-tert-butyl dicarbonate in a solvent such as acetonitrile at room temperature. Subsequently, the thiomorpholines can be oxidized with an oxidizing reagent such as 3-chloroperoxybenzoic acid, in a solvent such as dchloromethane, at temperatures between 0° C. and room temperature, to obtain thiomorpholine 1,1-dioxides (XI). After which the tert-butyloxycarbonyl (BOC) group can be removed by the treatment with an acid, such as hydrogen chloride, in a solvent such as ethanol, at temperatures between room temperature and 60° C., to afford modified thiomorpholine 1,1-dioxides (XII). Thiomorpholine 1,1-dioxides can then be reacted in a so called Michael reaction as described above for the thiomorpholines, to obtain compounds XIII (Q2=CH2CH2COOR'). In case compounds XIII are substituted with iodine (Q1=I), they can be substituted by a suitable phenol, in the presence of a base such as potassium phosphate tribasic, and catalyzed by a copper salt, such as copper(I) iodiode, and a suitable ligand, such as picolinic acid, in a solvent such as dimethylsulfoxide, at a temperature around 90° C., to obtain compounds XIII (W=SO₂, Q1=R1-A, Q2=CH2CH2COOR'). In case R' is tert-butyl acid hydrolysis as described for the thiomorpholines affords compounds (I, W=SO₂).

Abbreviations
ACE-Cl 1-Chloroethyl chloroformate
BINAP 2,2'-bis(diphenylphosphino)-1,1'-binaphthalene
BH₃.THF Borane tetrahydrofuran complex
n-BuLi n-Butyllithium
n-Bu₄NBr Tetrabutylammonium bromide
CD₃OD Methanol-d₄
CHCl₃ Chloroform
CDCl₃ Chloroform-d
CH₂Cl₂ Dichloromethane
CH₃CN Acetonitrile
Cs₂CO₃ Cesium carbonate
CuBr Copper(I) bromide
CuI Copper(I) iodide
DIPEA N,N-Diisopropylethylamine
DMF N,N-dimethylformamide
DMSO Dimethyl sulfoxide
Et₃N Triethylamine
Et₂O Diethyl ether
EtOH Ethanol
EtOAc Ethyl acetate
HCl Hydrogen chloride
K₂CO₃ Potassium carbonate
KF Potassium fluoride
KOH Potassium hydroxide
KOtBu Potassium tert-butoxide K₃PO₄ Potassium phosphate tribasic
LiAlH₄ Lithium aluminum hydride
LiHMDS Lithium bis(trimethylsilyl)amide
MeI Methyl iodide
MeMgBr Methylmagnesium bromide
MeOH Methanol
min. minutes
MgSO₄ Magnesium sulfate
NaBH₄ Sodium borohydride
NaH Sodium hydride
NaHCO₃ Sodium bicarbonate
NaI Sodium Iodide
NaN₃ Sodium azide
NaOH Sodium hydroxide
NaOtBu Sodium tert-butoxide
Na₂SO₄ Sodium sulfate
NBS N-Bromosuccinimide
NH₄Cl Ammonium chloride
NH₄OH Ammonium hydroxide
Pd₂(dba)₃ Tris(dibenzylideneacetone)dipalladium(0)
iPr₂O Diisopropyl ether
RT Room Temperature
SiO₂ Silica gel
TFA Trifluoroacetic acid
THF Tetrahydrofuran
TMSOTf Trimethylsilyl trifluoromethanesulfonate
Xantphos 4,5-Bis(diphenylphosphino)-9,9-dimethylxanthene
ZrCl4 Zirconium tetrachloride §3. Syntheses of Intermediates

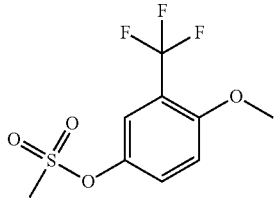 [SMILES: COc1ccc(OS(C)(=O)=O)cc1C(F)(F)F]

Methanesulfonic acid
4-acetyl-3-trifluoromethyl-phenyl ester

To a solution of 1-(4-hydroxy-2-trifluoromethyl-phenyl)-ethanone (29.74 g; 145.7 mmol) in CH₂Cl₂ (300 mL) and THF (120 mL) was added Et₃N (24.4 mL; 174.8 mmol), at 0° C. To the resulting mixture was added dropwise a solution of methanesulfonyl chloride (12.5 mL; 160.3 mmol) in CH₂Cl₂ (60 mL), at 0° C. Subsequently the mixture was stirred overnight at RT, and poured in ice-water. The layers were separated and the organic layer was washed with 1 M aqueous HCl and water; dried (MgSO₄), filtered and concentrated in vacuo to afford methanesulfonic acid 4-acetyl-3-trifluoromethyl-phenyl ester (40.47 g), which was used as such.

The following compounds were prepared in an analogues manner:
Methanesulfonic acid 4-acetyl-2-chloro-phenyl ester
Methanesulfonic acid 4-acetyl-3-fluoro-phenyl ester

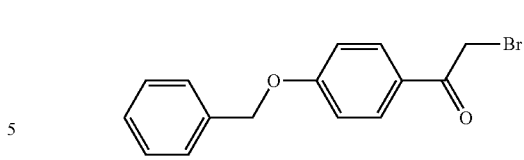

1-(4-Benzyloxy-phenyl)-2-bromo-ethanone

To a solution of 1-(4-(benzyloxy)-phenyl)-ethanone (49.12 g; 217.1 mmol) in CH₂Cl₂ (750 mL) was added drop wise DIPEA (45.37 mL; 260.5 mmol) and TMSOTf (45.18 mL; 249.6 mmol), both at 0° C. The resulting solution was maintained at 0° C. for 1 h, and then NBS (42.50 g; 238.8 mmol) was added in four portions. The resulting mixture was allowed to warm to RT and stirred 1 hour. Subsequently, the mixture was concentrated in vacuo and the residue was treated with EtOAc and washed twice with water, and brine. The organic layer was dried (MgSO₄), filtered and concentrated in vacuo. The residue was purified by column chromatography (SiO₂, Et₂O) and crystallization from iPr₂O to afford 1-(4-benzyloxy-phenyl)-2-bromo-ethanone.

The following compound was obtained according to a similar manner:
Methanesulfonic acid 4-(2-bromo-acetyl)-3-trifluoromethyl-phenyl ester
Methanesulfonic acid 4-(2-bromo-acetyl)-2-chloro-phenyl ester
Methanesulfonic acid 4-(2-bromo-acetyl)-3-fluoro-phenyl ester
1-(3-Benzyloxy-phenyl)-2-bromo-ethanone

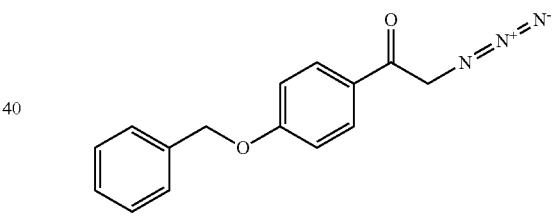

2-Azido-1-(4-benzyloxy-phenyl)-ethanone

To a mixture of 1-(4-benzyloxy-phenyl)-2-bromo-ethanone (28.55 g; 93.6 mmol) in CH₂Cl₂ (300 mL) and water (30 mL) was added nBu₄NBr (1.51 g; 4.7 mmol) and NaN₃ (6.69 g; 102.9 mmol) in one portion. After 4 h at RT, the layers were separated. The organic layer was washed water, dried (Na₂SO₄), filtered and concentrated in vacuo to afford 2-azido-1-(4-benzyloxy-phenyl)-ethanone (23.64 g)

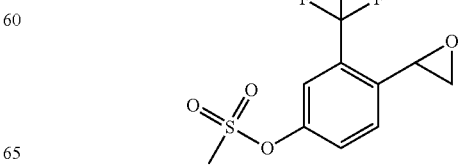

Methanesulfonic acid 4-oxiranyl-3-trifluoromethyl-phenyl ester

To a solution of methanesulfonic acid 4-(2-bromo-acetyl)-3-trifluoromethyl-phenyl ester (33.95 g; 89.3 mmol) in 1,4-dioxane (150 mL) was added dropwise a solution of NaBH$_4$ (2.37 g; 62.5 mmol) in water (47 mL). The resulting mixture was stirred at RT for 2.5 hours, subsequently, quenched with 0.5M aqueous HCl (125 mL), and extracted with EtOAc. The combined organic layers were washed with water, dried (MgSO$_4$), filtered and concentrated in vacuo. The residue was dissolved in Et$_2$O (500 mL) and treated with a solution of KOH (4.19 g; 74.7 mmol) in water (100 mL). The resulting mixture was heated under reflux for 4 hours. After cooling to RT, the volatiles were removed in vacuo and the residue was partitioned between EtOAc and water. The organic layer was washed with water, dried (MgSO$_4$), filtered and concentrated in vacuo. The residue was purified by column chromatography (CH$_2$Cl$_2$) to afford methanesulfonic acid 4-oxiranyl-3-trifluoromethyl-phenyl ester (23.54 g).

The following compounds were prepared in an analogues manner:

Methanesulfonic acid 4-oxiranyl-3-fluoro-phenyl ester

Methanesulfonic acid 4-oxiranyl-2-chloro-phenyl ester

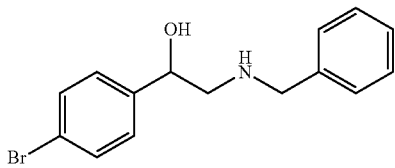 [SMILES: OC(CNCc1ccccc1)c1ccc(Br)cc1]

2-Benzylamino-1-(4-bromo-phenyl)-ethanol

To a cooled (0° C.) suspension of 2-bromo-1-(4-bromophenyl)ethanone (40.24 g; 0.14 mol) in EtOH (500 mL) and CHCl$_3$ (100 mL) was added benzylamine (63 mL; 0.58 mol). After 30 minutes the ice-bath was removed and the mixture stirred for another 2 hours at RT. Subsequently the reaction mixture was cooled again to 0° C. and NaBH$_4$ (6.26 g; 165.5 mmol) was added in small portions. The resulting mixture was stirred at 0° C. for 1 hour and thereafter another 4 hours at RT. The reaction mixture was quenched with 1M aqueous HCl (750 mL) at 0° C. and stirred at RT for 1 hour. The reaction mixture was concentrated in vacuo and the residue was partitioned between EtOAc and 1M aqueous NaOH. The organic layer was dried (Na$_2$SO$_4$), filtered, concentrated in vacuo. The residue was crystallized from tort-butyl methyl ether/heptanes to afford 2-benzylamino-1-(4-bromo-phenyl)-ethanol (18.8 g).

The following compound was obtained according to a similar manner:

2-Benzylamino-1-(4-benzyloxy-phenyl)-ethanol

2-Benzylamino-1-(3-benzyloxy-phenyl)-ethanol

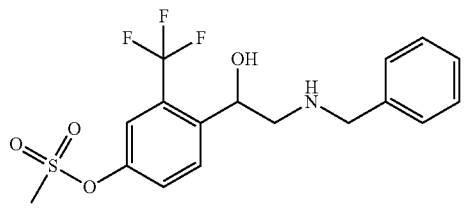 [SMILES: CS(=O)(=O)Oc1ccc(C(O)CNCc2ccccc2)c(C(F)(F)F)c1]

Methanesulfonic acid 4-(2-benzylamino-1-hydroxyethyl)-3-trifluoromethyl-phenyl ester Methanesulfonic acid 4-oxiranyl-3-trifluoromethyl-phenyl ester (23.54 g; 79.2 mmol) was dissolved in benzylamine (26 mL). The resulting mixture was stirred at 80° C. for 4 h. After cooling to RT, Et$_2$O was added and the mixture cooled to 0° C. The formed precipitate was collected by filtration, washed with Et$_2$O, and dried under vacuum, at 40° C., to afford methanesulfonic acid 4-(2-benzylamino-1-hydroxyethyl)-3-trifluoromethyl-phenyl ester as a white solid (26.87 g) which was used as such.

The following compounds were prepared in a similar manner:

Methanesulfonic acid 4-(2-benzylamino-1-hydroxyethyl)-3-fluoro-phenyl ester

Methanesulfonic acid 4-(2-benzylamino-1-hydroxyethyl)-2-chloro-phenyl ester

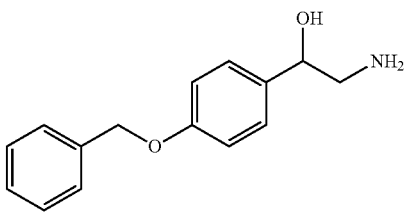 [SMILES: NCC(O)c1ccc(OCc2ccccc2)cc1]

2-Amino-1-(4-benzyloxy-phenyl)-ethanol

To a suspension of LiAlH$_4$ (8.18 g; 215.6 mmol) in THF (100 mL), was added dropwise a solution of 2-azido-1-(4-benzyloxy-phenyl)-ethanone (23.05 g; 86.2 mmol) in THF (200 mL), at 0° C. The mixture was stirred at 0° C. for 20 min. and subsequently 2 hours at RT. Thereafter, water (50 mL), and 2M aqueous NaOH-solution (150 mL) were added consecutively. The formed precipitate was removed by filtration over kieselguhr, and washed with MeOH. The filtrate was concentrated in vacuo and the remaining aqueous layer was extracted with CH$_2$Cl$_2$. The combined organic layers were dried (Na$_2$SO$_4$), filtered and concentrated in vacuo to afford 2-amino-1-(4-benzyloxy-phenyl)-ethanol (20.10 g).

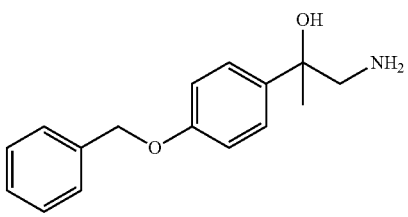 [SMILES: CC(O)(CN)c1ccc(OCc2ccccc2)cc1]

1-Amino-2-(4-benzyloxy-phenyl)-propan-2-ol

A mixture of 1-(4-benzyloxy-phenyl)-ethanone (18.50 g; 81.8 mmol), zinc iodide (0.52 g; 1.6 mmol), and trimethylsilyl cyanide (33.8 mL; 269.8 mmol) was stirred overnight at RT. Subsequently, the excess trimethylsilyl cyanide was removed in vacuo, and the residue dissolved in THF (100 mL). The resulting solution was added, dropwise, to a mixture of LiAlH₄ (12.7 g; 335.2 mmol) in THF (200 mL). The resulting mixture was heated under reflux for 2 h. Next, the mixture was cooled to 0° C. and treated successively with water (13 mL), 2M aqueous NaOH (26 mL), and water (13 mL). Thereafter the mixture was heated under reflux for 15 minutes, cooled again to RT, filtered over Kieselguhr, and concentrated in vacuo. The residue was purified by column chromatography (SiO₂, MeOH) to afford 1-Amino-2-(4-benzyloxy-phenyl)-propan-2-ol (18.15 g).

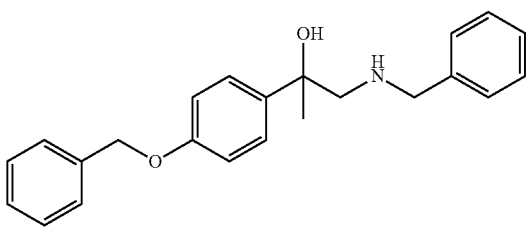 [SMILES: CC(O)(CNCc1ccccc1)c1ccc(OCc2ccccc2)cc1]

1-Benzylamino-2-(4-benzyloxy-phenyl)-propan-2-ol

A mixture of 1-amino-2-(4-benzyloxy-phenyl)-propan-2-ol (1.26 g; 4.9 mmol), benzaldehyde (0.55 mL; 5.4 mmol), and p-toluenesulfonic acid (0.04 g; 0.24 mmol) in toluene (30 mL) was heated under reflux in a Dean-Stark apparatus, overnight. Subsequently, the mixture was cooled to RT and the solvent was removed in vacuo. The residue was suspended in MeOH (30 mL), cooled to −15° C., and treated with NaBH₄ (0.74 g; 19.6 mmol), portionwise. After the addition was complete the mixture was warmed to RT and stirred for one hour. Subsequently, the MeOH was removed in vacuo. The residue was partitioned between Et₂O and 5% aqueous NaHCO₃. The organic layer was dried (Na₂SO₄), filtered, and concentrated in vacuo. The residue was purified by column chromatography (SiO₂, Et₂O: hexanes 2:1) to give 1-benzylamino-2-(4-benzyloxy-phenyl)-propan-2-ol (1.07 g).

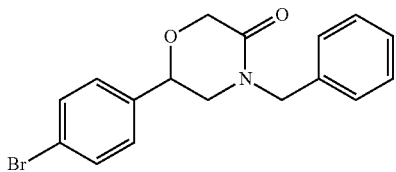 [SMILES: O=C1COC(c2ccc(Br)cc2)CN1Cc1ccccc1]

4-Benzyl-6-(4-bromo-phenyl)-morpholin-3-one

To a solution of 2-benzylamino-1-(4-bromo-phenyl)-ethanol (18.95 g; 62 mmol) and Et₃N (9.6 mL; 68 mmol) in CH₂Cl₂ (500 mL) was added dropwise a solution of chloroacetyl chloride (5.4 mL; 68 mmol) in CH₂Cl₂ (20 mL), at 0° C. After 1 hour at 0° C. the reaction mixture was quenched with 1M aqueous HCl (200 mL). The layers were separated and the organic layer washed with a 5% aqueous NaHCO₃ solution, dried (Na₂SO₄) and concentrated in vacuo. The residue was dissolved in 2-propanol (200 mL) and KOH (4.2 g; 75 mmol) was added. The resulting mixture was stirred at RT for 3 hours and subsequently concentrated in vacuo. The crude product was partitioned between CH₂Cl₂ and 1M aqueous HCl. The layers were separated and the organic layer was washed with saturated aqueous NaHCO₃ solution, dried (Na₂SO₄) and evaporated in vacuo to afford 4-benzyl-6-(4-bromo-phenyl)-morpholin-3-one (22.30 g) which was used as such in the next step.

The following compound was obtained according to a similar manner:
  4-Benzyl-6-(4-benzyloxy-phenyl)-morpholin-3-one
  4-Benzyl-6-(3-benzyloxy-phenyl)-morpholin-3-one
  4-Benzyl-6-(4-benzyloxy-phenyl)-6-methyl-morpholin-3-one The following compounds were obtained according to a similar manner from methanesulfonic acid phenyl esters using 2.5 equivalents of KOH instead of 1.25 equivalents:
  4-Benzyl-6-(4-hydroxy-2-trifluoromethyl-phenyl)-morpholin-3-one
  4-Benzyl-6-(2-fluoro-4-hydroxy-phenyl)-morpholin-3-one
  4-Benzyl-6-(3-chloro-4-hydroxy-phenyl)-morpholin-3-one

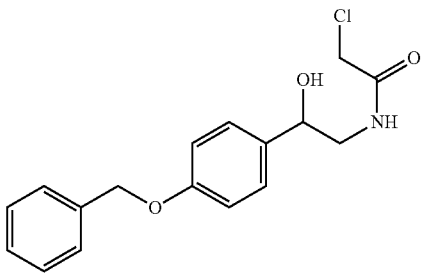 [SMILES: O=C(CCl)NCC(O)c1ccc(OCc2ccccc2)cc1]

N-[2-(4-Benzyloxy-phenyl)-2-hydroxy-ethyl]-2-chloro-acetamide

To a mixture of 2-amino-1-(4-benzyloxy-phenyl)-ethanol (20.10 g; 82.6 mmol), Et₃N (13.82 mL; 99.1 mmol), CH₂Cl₂ (200 mL) and MeOH (20 mL) was added dropwise chloroacetyl chloride (7.24 mL; 90.9 mmol) at −10° C. The resulting mixture was allowed to warm to RT and stirred overnight, and subsequently concentrated in vacuo. The residue was purified by flash chromatography (SiO₂, EtOAc) to afford N-[2-(4-benzyloxy-phenyl)-2-hydroxy-ethyl]-2-chloro-acetamide (17.45 g).

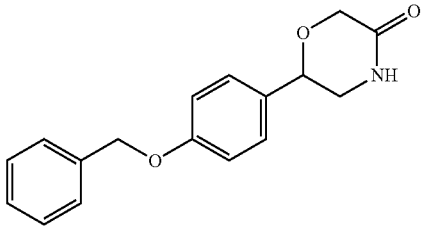 [SMILES: O=C1COC(c2ccc(OCc3ccccc3)cc2)CN1]

6-(4-Benzyloxy-phenyl)-morpholin-3-one

To a solution of KOtBu (6.68 g; 59.5 mmol) in 2-methyl-2-butanol (100 mL) was added dropwise a solution of N-[2-

(4-benzyloxy-phenyl)-2-hydroxy-ethyl]-2-chloro-acetamide (17.30 g; 54.1 mmol) in THF (100 mL). The resulting mixture was stirred for 1 hour at RT and then concentrated in vacuo. The residue was dissolved in CH₂Cl₂ and treated with a 1M aqueous solution of HCl, at 0° C. The layers were separated and the aqueous layer extracted with CH₂Cl₂. The combined organic layers were dried (Na₂SO₄), filtered and concentrated in vacuo to afford 6-(4-benzyloxy-phenyl)-morpholin-3-one (14.10 g).

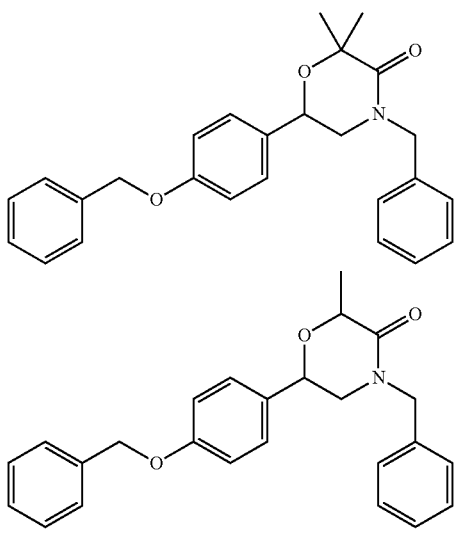

4-Benzyl-6-(4-benzyloxy-phenyl)-2,2-dimethyl-morpholin-3-one and 4-Benzyl-6-(4-benzyloxy-phenyl)-2-methyl-morpholin-3-one To a solution of 4-benzyl-6-(4-benzyloxy-phenyl)-morpholin-3-one (6.90 g; 18.5 mmol) in THF (100 mL) was added dropwise a solution of LiHMDS in THF (18.5 mL; 1.00 mol/l; 18.5 mmol), at −78° C. The resulting mixture was stirred at −78° C. for 15 minutes, subsequently, MeI (1.15 mL; 18.5 mmol) was added, and the resulting mixture stirred for 1 hour at −78° C. The sequence of addition of LiHMDS and MeI, was repeated three times. After the last addition of MeI the mixture was allowed to warm to RT and stirred overnight. Then an 5% aqueous NaHCO₃ solution was added en the mixture extracted with EtOAc. The combined organic layers were dried (Na₂SO₄), filtered and concentrated in vacuo. The residue was purified by column chromatography (SiO₂, Et₂O/hexanes 1:1) to afford two compounds. The least polar compound was 4-benzyl-6-(4-benzyloxy-phenyl)-2,2-dimethyl-morpholin-3-one (1.90 g), and the most polar compound was 4-benzyl-6-(4-benzyloxy-phenyl)-2-methyl-morpholin-3-one (3.81 g).

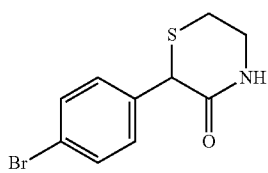 [SMILES: O=C1NCCSC1c1ccc(Br)cc1]

2-(4-Bromo-phenyl)-thiomorpholin-3-one

To a solution of 2-aminoethanethiol hydrochloride (6.93 g; 61 mmol) in EtOH (400 mL) was added K₂CO₃ (16.86 g; 122 mmol), at RT, followed after 15 minutes by bromo-(4-bromo-phenyl)-acetic acid ethyl ester (12 mL; 61 mmol). The resulting mixture was stirred at RT for two days, subsequently, water was added and the resulting mixture was extracted with EtOAc. The combined organic layers were dried (MgSO₄), filtered, and concentrated in vacuo. The residue was recrystallized from EtOH to afford 2-(4-bromo-phenyl)-thiomorpholin-3-one (12.8 g).

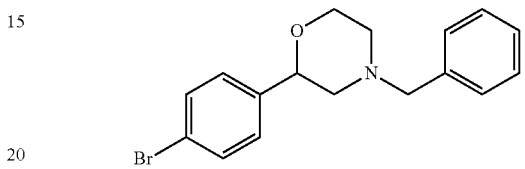

4-Benzyl-6-(4-bromo-phenyl)-morpholine

To a solution of 4-benzyl-6-(4-bromo-phenyl)-morpholin-3-one (21.3 g; 62 mmol) in THF (350 mL) was added BH₃.THF in THF (1M, 155 mL; 155 mmol) dropwise, at 0° C. After 1 hour the mixture was allowed to warm to RT and stirred for another 2 hours. To the reaction mixture was added MeOH (300 mL), at 0° C., the resulting mixture was stirred at RT for 3 days, and subsequently concentrated in vacuo. The residue was partitioned between EtOAc and 1 M aqueous NaOH-solution. The organic layer was dried (Na₂SO₄), filtered, and concentrated in vacuo to afford 4-benzyl-2-(4-bromo-phenyl)-morpholine (20.1 g), which was used as such in the next step.

The following compound was obtained according to a similar manner:
4-Benzyl-2-(4-benzyloxy-phenyl)-morpholine
4-Benzyl-2-(3-benzyloxy-phenyl)-morpholine
4-Benzyl-2-(4-benzyloxy-phenyl)-2-methyl-morpholine
4-Benzyl-6-(4-benzyloxy-phenyl)-2,2-dimethyl-morpholine

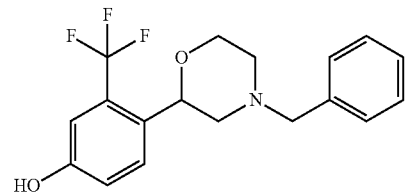 [SMILES: Oc1ccc(C2CN(Cc3ccccc3)CCO2)c(C(F)(F)F)c1]

4-(4-Benzyl-morpholin-2-yl)-3-trifluoromethyl-phenol

To a solution of 4-benzyl-6-(4-hydroxy-2-trifluoromethyl-phenyl)-morpholin-3-one (26.18 g; 67.3 mmol) in THF (600 mL) was added dropwise BH₃.THF in THF (235.4 mL; 1.00 mold; 235.4 mmol), at 0° C. The resulting mixture was stirred for 1 hour at 0° C. and thereafter 18 hours at RT. Subsequently, 1M aqueous HCl (550 mL) was added and the mixture stirred overnight at RT. The resulting mixture was partitioned between EtOAc and 2M aqueous NaOH (350 mL), the organic layers was dried (MgSO₄), filtered, and concentrated in vacuo. The residue was purified by column chromatography (SiO$_2$, CH$_2$Cl$_2$/MeOH 98:2) to afford 4-(4-benzyl-morpholin-2-yl)-3-trifluoromethyl-phenol The following compounds were obtained according to a similar manner:

4-(4-Benzyl-morpholin-2-yl)-3-fluoro-phenol 2-(4-Bromo-phenyl)-thiomorpholine

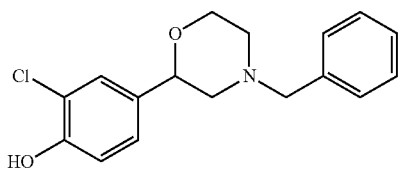 [SMILES: Oc1ccc(C2CN(Cc3ccccc3)CCO2)cc1Cl]

4-(4-Benzyl-morpholin-2-yl)-2-chloro-phenol

To a solution of 4-benzyl-6-(3-chloro-4-hydroxy-phenyl)-morpholin-3-one (13.05 g; 39.0 mmol) in THF (600 mL) was added portionwise LiAlH$_4$ (4.44 g; 117.04 mmol) at 0° C. The resulting mixtures was allowed to warm to RT and stirred overnight. Subsequently, the mixture was cooled to 0° C., and water (4.5 mL), a 2M aqueous NaOH-solution (9.0 mL) and water (9.0 mL) were added consecutively. Thereafter the mixture was stirred for 1 h. The formed precipitate was removed by filtration over kieselguhr, and washed with EtOAc. The organic solution was concentrated in vacuo, and the residue purified by column chromatography (SiO$_2$, CH$_2$Cl$_2$/MeOH 98:2) to afford 4-(4-benzyl-morpholin-2-yl)-2-chloro-phenol (9.10 g)

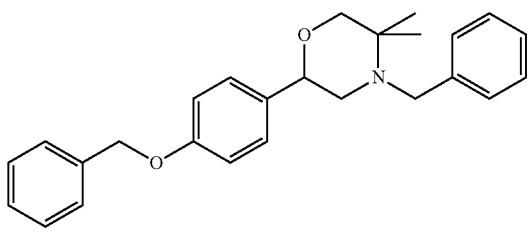 [SMILES: CC1(C)COC(c2ccc(OCc3ccccc3)cc2)CN1Cc1ccccc1]

4-Benzyl-2-(4-benzyloxy-phenyl)-5,5-dimethyl-morpholine

To a solution of 4-benzyl-6-(4-benzyloxy-phenyl)-morpholin-3-one (7.14 g; 19.1 mmol) in THF (100 mL) was added ZrCl$_4$ (4.46 g; 19.1 mmol), at −10° C. The resulting mixture was stirred for 30 min. at −10° C., subsequently, a solution of MeMgBr in Et$_2$O (38.2 mL; 3.00 mol/l; 114.6 mmol) was added dropwise, keeping the temperature below 10° C. After complete addition the resulting mixture was stirred at RT for 1 hour. After cooling the mixture to 0° C. a 2M aqueous NaOH solution was added dropwise. The resulting suspension was filtered and the filtrate was extracted three times with CH$_2$Cl$_2$. The combined organic layers were dried (Na$_2$SO$_4$), filtered, and concentrated in vacuo. The residue was purified by column chromatography (SiO$_2$, Et$_2$O/hexanes 1:3) to afford 4-benzyl-2-(4-benzyloxy-phenyl)-5,5-dimethyl-morpholine (3.6 g).

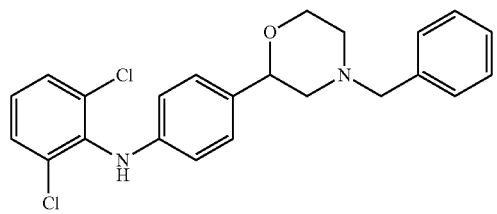 [SMILES: Clc1cccc(Cl)c1Nc1ccc(C2CN(Cc3ccccc3)CCO2)cc1]

[4-(4-Benzyl-morpholin-2-yl)-phenyl]-(2,6-dichloro-phenyl)-amine

To a solution of BINAP (112.45 mg; 0.18 mmol) in degassed toluene (20 mL) was added 4-benzyl-2-(4-bromo-phenyl)-morpholine (1.00 g; 3.01 mmol), 2,6-dichloroaniline (0.49 g; 3.01 mmol), Pd$_2$(dba)$_3$ (55.12 mg; 0.06 mmol) and NaOtBu (0.29 g; 3.01 mmol). The resulting mixture was heated at 100° C. for 18 h. After cooling to RT the resulting mixture was filtered over kieselguhr, rinsed with CH$_2$Cl$_2$, and concentrated in vacuo. The residue was purified by column chromatography (Et$_2$O:hexanes 1:3) to afford [4-(4-benzyl-morpholin-2-yl)-phenyl]-(2,6-dichloro-phenyl)-amine (0.73 g).

The following compound was obtained according to a similar manner:

[4-(4-Benzyl-morpholin-2-yl)-phenyl]-(2,6-dimethyl-phenyl)-amine.

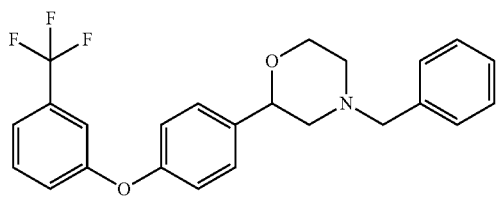 [SMILES: FC(F)(F)c1cccc(Oc2ccc(C3CN(Cc4ccccc4)CCO3)cc2)c1]

4-Benzyl-2-[4-(3-trifluoromethyl-phenoxy)-phenyl]-morpholine

A mixture of 4-benzyl-2-(4-bromo-phenyl)-morpholine (1.5 g, 4.6 mmol), 3-(trifluoromethyl)phenol (0.83 mL, 6.8 mmol), copper(I) iodide (438 mg, 2.3 mmol), 2,2,6,6-tetramethyl-3,5-heptanedione (0.48 mL, 2.3 mmol), and cesium carbonate (2.96 g, 9.1 mmol), in toluene (20 mL) was heated under reflux for 3 days. After cooling to room temperature, the mixture was partitioned between EtOAc and water. The layers were separated. The organic layer was dried (Na$_2$SO$_4$), filtered and concentrated in vacuo. The residue was purified by column chromatography (EtOAc:heptanes 5:95) to afford 4-benzyl-2-[4-(3-trifluoromethyl-phenoxy)-phenyl]-morpholine (0.9 g), which was used as such in the next step.

The following compound was made in a similar manner:

4-Benzyl-2-[4-(2-methyl-phenoxy)-phenyl]-morpholine

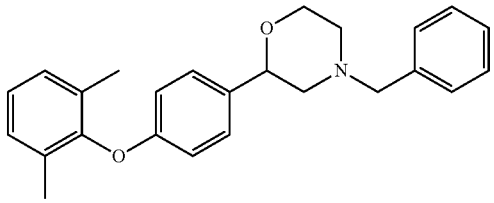 [SMILES: Cc1cccc(C)c1Oc1ccc(C2CN(Cc3ccccc3)CCO2)cc1]

4-Benzyl-2-[4-(2,6-dimethyl-phenoxy)-phenyl]-morpholine 2,6-Dimethylphenol was added portionwise to a suspension of NaH (272 mg, 60% in oil, 6.8 mmol) in toluene (15 mL). After complete addition the mixture was heated under reflux for 15 min. and subsequently cooled to room temperature. To the resulting mixture was added a solution of 4-benzyl-2-(4-bromo-phenyl)-morpholine (1.5 g, 4.5 mmol) in toluene (10 mL), followed by copper(I) iodide (438 mg, 2.3 mmol), 2,2,6,6-tetramethyl-3,5-heptanedione (0.48 mL, 2.3 mmol), and cesium carbonate (2.96 g, 9.1 mmol). The obtained mixture was heated under reflux for 3 days. After cooling to room temperature, the mixture was partitioned between EtOAc and water. The layers were separated. The organic layer was dried (Na$_2$SO$_4$), filtered and concentrated in vacuo. The residue was purified by column chromatography (EtOAc:heptanes 5:95) to afford 4-benzyl-2-[4-(2,6-dimethyl-phenoxy)-phenyl]-morpholine (1.2 g), which was used as such in the next step.

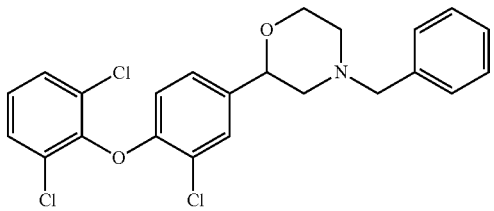 [SMILES: Clc1cc(C2CN(Cc3ccccc3)CCO2)ccc1Oc1c(Cl)cccc1Cl]

4-Benzyl-2-[3-chloro-4-(2,6-dichloro-phenoxy)-phenyl]-morpholine

A solution of 4-(4-benzyl-morpholin-2-yl)-2-chloro-phenol (0.50 g; 1.56 mmol), 2,6-dichlorofluorobenzene (0.26 g; 1.56 mmol) and K$_2$CO$_3$ (0.32 g; 2.35 mmol) in DMF (10 mL) was heated at 100° C. for three days. After cooling to RT, the mixture was diluted with EtOAc and washed with water (3×). The organic layer was dried (MgSO$_4$), filtered, and concentrated in vacuo. The residue was purified by column chromatography (SiO$_2$, CH$_2$Cl$_2$/MeOH 99.5:0.5) to afford 4-Benzyl-2-[3-chloro-4-(2,6-dichloro-phenoxy)-phenyl]-morpholine (0.35 g).

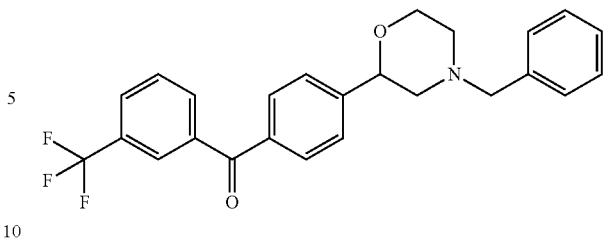

[4-(4-Benzyl-morpholin-2-yl)-phenyl]-(3-trifluoromethyl-phenyl)-methanone

To a solution of 4-benzyl-2-(4-bromo-phenyl)-morpholine (1.89 g, 5.7 mmol) in THF (30 mL), at −78° C., was added dropwise n-butyl lithium (2.85 mL; 2.5 mol/l in hexanes; 7.1 mmol). The mixture was stirred for 20 min. at −78° C., and subsequently N-Methoxy-N-methyl-3-trifluoromethyl-benzamide (2.66 g, 11.4 mmol) was added. The mixture was allowed to warm to RT and stirred overnight. The resulting mixture was partitioned between an aqueous saturated NH$_4$Cl solution and EtOAc. The layers were separated. The organic layer was washed with a saturated aqueous NaHCO$_3$-solution, dried (Na$_2$SO$_4$), filtered and concentrated in vacuo. The residue was purified by column chromatography (EtOAc:heptanes 1:3) to afford [4-(4-benzyl-morpholin-2-yl)-phenyl]-(3-trifluoromethyl-phenyl)-methanone (0.84 g), which was used as such in the next step.

The following compound was made in a similar manner:

[4-(4-Benzyl-morpholin-2-yl)-phenyl]-o-tolyl-methanone

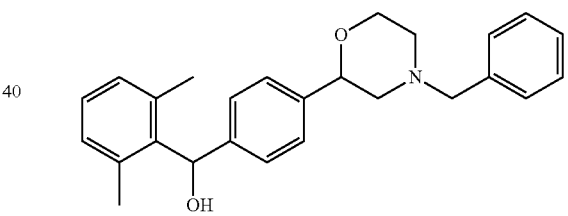

[4-(4-Benzyl-morpholin-2-yl)-phenyl]-(2,6-dimethyl-phenyl)-methanol

To a solution of 4-benzyl-2-(4-bromo-phenyl)-morpholine (2.1 g, 6.3 mmol) in THF (30 mL), at −78° C., was added dropwise t-butyl lithium (7.9 mL; 1.6 mol/l in heptanes; 12.6 mmol). The mixture was stirred for 20 min. at −78° C., and subsequently 2,6-dimethylbenzaldehyde (1 g, 7.6 mmol) was added. The mixture was allowed to warm to RT and stirred overnight. The resulting mixture was partitioned between water and EtOAc. The layers were separated. The organic layer was washed with water, dried (Na$_2$SO$_4$), filtered and concentrated in vacuo. The residue was purified by column chromatography (EtOAc:heptanes 1:1) to afford [4-(4-benzyl-morpholin-2-yl)-phenyl]-(2,6-dimethyl-phenyl)-methanol (1.6 g), which was used as such in the next step.

The following compound was made in a similar manner:

[4-(4-Benzyl-morpholin-2-yl)-phenyl]-(2,6-dichloro-phenyl)-methanol

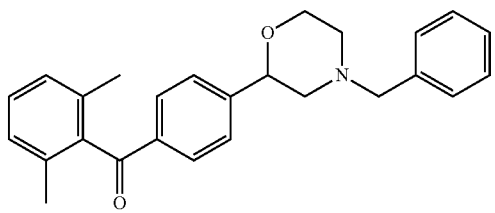 [SMILES: Cc1cccc(C)c1C(=O)c1ccc(C2CN(Cc3ccccc3)CCO2)cc1]

[4-(4-Benzyl-morpholin-2-yl)-phenyl]-(2,6-dimethyl-phenyl)-methanone

To a solution of oxalyl chloride (0.46 mL, 5.4 mmol) in CH$_2$Cl$_2$ (20 mL), was added dropwise DMSO (0.94 mL, 13.2 mmol), at −78° C. Subsequently, a solution of [4-(4-benzyl-morpholin-2-yl)-phenyl]-(2,6-dimethyl-phenyl)-methanol (1.6 g, 4.1 mmol) in CH$_2$Cl$_2$ (30 mL) was added, dropwise, at −78° C. After the addition was complete the mixture was stirred for 30 min., at −78° C., and then Et$_3$N (2.9 mL, 20.8 mmol) was added. After complete addition the mixture was allowed to warm to room temperature, overnight. Next, a 2M aqueous NH$_4$OH solution (30 mL) was added, and the mixture extracted with CH$_2$Cl$_2$. The combined organic layers were dried (Na$_2$SO$_4$), filtered and concentrated in vacuo to afford [4-(4-benzyl-morpholin-2-yl)-phenyl]-(2,6-dimethyl-phenyl)-methanone (1.5 g), which was used as such in the next step.

The following compound was made in a similar manner:

[4-(4-Benzyl-morpholin-2-yl)-phenyl]-(2,6-dichloro-phenyl)-methanone

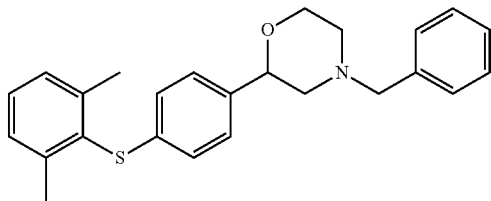

4-Benzyl-2-[4-(2,6-dimethyl-phenylsulfanyl)-phenyl]-morpholine

To a solution of 4-benzyl-2-(4-bromo-phenyl)-morpholine (2.00 g; 6.02 mmol) and 2,6-dimethylthiophenol (0.88 mL; 6.62 mmol) in DMF (15 mL) was added CuBr (0.43 g; 3.01 mmol), 1,2,3,4-tetrahydro-quinolin-8-ol (0.45 g; 3.01 mmol) and Cs$_2$CO$_3$ (2.45 g; 7.52 mmol; 1.25 eq.). The resulting mixture was heated, in a closed vessel, at 130° C., for 2 days. After cooling to RT, water was added and the mixture extracted with Et$_2$O. The combined organic layers were washed with water, dried (Na$_2$SO$_4$), filtered and concentrated in vacuo. The residue was purified by column chromatography (Et$_2$O/hexanes 1:1) to afford 4-benzyl-2-[4-(2,6-dimethyl-phenylsulfanyl)-phenyl]-morpholine (1.60 g).

The following compounds were made in a similar manner:

4-Benzyl-2-[4-(2,3-dichloro-phenylsulfanyl)-phenyl]-morpholine

4-Benzyl-2-(4-o-tolylsulfanyl-phenyl)-morpholine

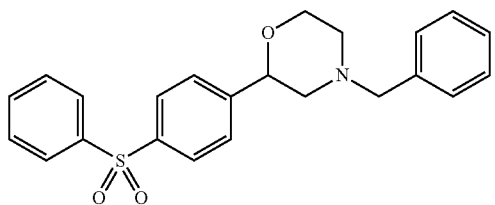 [SMILES: O=S(=O)(c1ccccc1)c1ccc(C2CN(Cc3ccccc3)CCO2)cc1]

2-(4-Benzenesulfonyl-phenyl)-4-benzyl-morpholine

To a degassed mixture of 4-benzyl-6-(4-bromo-phenyl)-morpholine (0.45 g; 1.35 mmol), sodium benzenesulfinate (0.27 g; 1.63 mmol), Cs$_2$CO$_3$ (0.66 g; 2.03 mmol), and tetrabutylammonium chloride (0.45 g; 1.63 mmol) in toluene (10 mL), was added Pd$_2$dba$_3$ (31.01 mg; 0.03 mmol) and Xantphos (39.19 mg; 0.07 mmol). The resulting mixture was heated under reflux for 2 days. After cooling to RT, EtOAc and a 5% aqueous NaHCO$_3$ solution were added. The layers were separated and the organic layer was dried (Na$_2$SO$_4$), filtered and concentrated in vacuo. The residue was purified by column chromatography (SiO$_2$, Et$_2$O) to afford 2-(4-benzenesulfonyl-phenyl)-4-benzyl-morpholine (0.28 g).

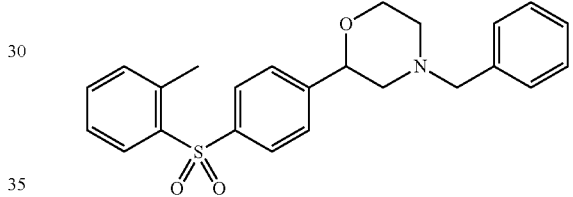

4-Benzyl-2-[4-(toluene-2-sulfonyl)-phenyl]-morpholine

To a solution of 4-benzyl-6-(4-bromo-phenyl)-morpholine (0.55 g; 1.66 mmol) in THF (25 mL) was added drop wise a solution of n-BuLi in hexanes (1.32 ml; 2.50 mol/l; 3.31 mmol), at −78° C. The resulting mixture was stirred at −78° C., for 30 min. and then 2-methyl-benzenesulfonyl fluoride (0.63 g; 3.64 mmol) was added. After complete addition the mixture was allowed to come to room temperature, and treated with EtOAc and a 5% aqueous NaHCO$_3$-solution. The layers were separated and the organic layer was dried (Na$_2$SO$_4$), filtered, and concentrated in vacuo. The residue was purified by column chromatography (SiO$_2$, Et$_2$O) to afford 4-benzyl-2-[4-(toluene-2-sulfonyl)-phenyl]-morpholine (0.50 g). The required 2-methyl-benzenesulfonyl fluoride was prepared as follows: To a solution of o-toluenesulfonyl chloride (0.70 mL; 4.85 mmol) in CH$_3$CN (15 mL) was added spray-dried KF (1.13 g; 19.4 mmol). The resulting mixture was stirred at RT for 18 hours, treated with water and extracted with CH$_2$Cl$_2$. The combined organic layers were dried (Na$_2$SO$_4$), filtered and concentrated in vacuo to afford 2-methyl-benzenesulfonyl fluoride (0.68 g).

The following compounds were made according to a similar method:

4-Benzyl-2-[4-(2-chloro-benzenesulfonyl)-phenyl]-morpholine

4-Benzyl-2-[4-(2,6-dichloro-benzenesulfonyl)-phenyl]-morpholine

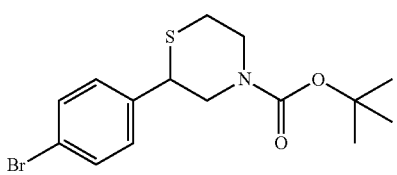 [SMILES: CC(C)(C)OC(=O)N1CCSC(c2ccc(Br)cc2)C1]

2-(4-Bromo-phenyl)-thiomorpholine-4-carboxylic acid tert-butyl ester

To a solution of 2-(4-bromo-phenyl)-thiomorpholine (2.80 g; 10.85 mmol) in CH$_2$Cl$_2$ (50 mL) was added di-tert-butyl dicarbonate (2.60 g; 11.93 mmol), at 0° C. After complete addition the mixture was allowed to warm to RT, and stirred overnight. Subsequently, the solvent was removed in vacuo and the residue purified by column chromatography (SiO$_2$, CH$_2$Cl$_2$) to afford 2-(4-bromo-phenyl)-thiomorpholine-4-carboxylic acid tert-butyl ester (3.61 g).

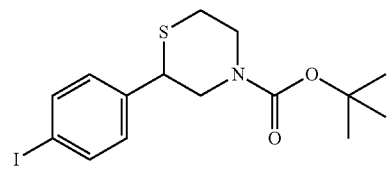 [SMILES: CC(C)(C)OC(=O)N1CCSC(c2ccc(I)cc2)C1]

2-(4-Iodo-phenyl)-thiomorpholine-4-carboxylic acid tert-butyl ester

To a degassed solution of 2-(4-bromo-phenyl)-thiomorpholine-4-carboxylic acid tert-butyl ester (0.75 g; 2.09 mmol) and N,N'-dimethylethylenediamine (0.11 mL; 1.05 mmol) in 1,4-dioxane (10 mL) was added CuI (39.9 mg; 0.21 mmol) and NaI (0.78 g; 5.23 mmol). The resulting mixture was heated in a closed vessel, at 130° C., for 3 days. After cooling to room temperature the mixture was concentrated in vacuo, and the residue was purified by column chromatography (SiO$_2$, CH$_2$Cl$_2$/hexanes 1:1) to afford 2-(4-iodo-phenyl)-thiomorpholine-4-carboxylic acid tert-butyl ester (0.35 g).

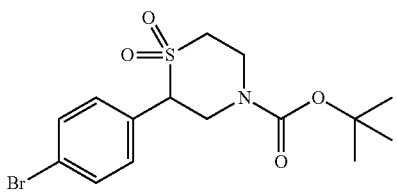 [SMILES: CC(C)(C)OC(=O)N1CCS(=O)(=O)C(c2ccc(Br)cc2)C1]

2-(4-Bromo-phenyl)-1,1-dioxo-1λ$^6$-thiomorpholine-4-carboxylic acid tert-butyl ester To a solution of 2-(4-bromo-phenyl)-thiomorpholine-4-carboxylic acid tert-butyl ester (3.60 g; 10.05 mmol) in CH$_2$Cl$_2$ (100 mL) was added 3-chloroperoxybenzoic acid (5.20 g; 30.14 mmol), at 0° C. The resulting mixture was stirred overnight at RT, and subsequently, a saturated aqueous sodium thiosulfate solution was added and the mixture stirred for another 30 min. The layers were separated and the aqueous layer was extracted twice with EtOAc. The combined EtOAc layers were washed twice with an aqueous Na$_2$CO$_3$ solution. The combined organic layers were dried (MgSO$_4$), filtered and concentrated in vacuo to afford 2-(4-Bromo-phenyl)-1,1-dioxo-1λ$^6$-thiomorpholine-4-carboxylic acid tert-butyl ester (4.06 g) which was used as such in the next step.

The following compound was made in a similar manner:
2-(4-Iodo-phenyl)-1,1-dioxo-1λ$^6$-thiomorpholine-4-carboxylic acid tert-butyl ester

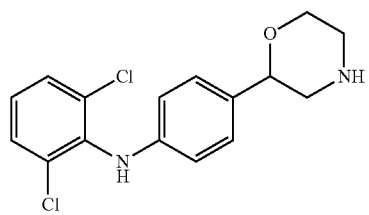 [SMILES: Clc1cccc(Cl)c1Nc1ccc(C2CNCCO2)cc1]

(2,6-Dichloro-phenyl)-(4-morpholin-2-yl-phenyl)-amine

To a solution of [4-(4-benzyl-morpholin-2-yl)-phenyl]-(2,6-dichloro-phenyl)-amine (0.72 g; 1.74 mmol) in 1,2-dichloroethane (5 mL) was added, drop wise, ACE-Cl (0.40 mL; 3.66 mmol) at 0° C. The resulting mixture was stirred at room temperature, overnight, and subsequently concentrated in vacuo. To the residue was added toluene and the mixture was concentrated in vacuo. This last step was repeated twice. To the final residue was added MeOH (5 mL), and this mixture was stirred overnight at RT. Once more the mixture was concentrated in vacuo. The residue was partitioned between EtOAc and 2 M Aqueous NaOH. The layers were separated, and the organic layer dried (Na$_2$SO$_4$), filtered, and concentrated in vacuo to afford (2,6-dichloro-phenyl)-(4-morpholin-2-yl-phenyl)-amine (0.34 g); which was used as such.

The following compounds were made in a similar manner:
(2,6-Dimethyl-phenyl)-(4-morpholin-2-yl-phenyl)-amine
[4-(4-Morpholin-2-yl)-phenyl]-(3-trifluoromethyl-phenyl)-methanone
(2,6-Dimethyl-phenyl)-(4-morpholin-2-yl-phenyl)-methanone
2-[4-(3-Trifluoromethyl-phenoxy)-phenyl]-morpholine
2-(4-o-Tolyloxy-phenyl)-morpholine
2-[4-(2,6-Dimethyl-phenoxy)-phenyl]-morpholine
(4-Morpholin-2-yl-phenyl)-o-tolyl-methanone
(2,6-Dichloro-phenyl)-(4-morpholin-2-yl-phenyl)-methanone
2-[3-Chloro-4-(2,6-dichloro-phenoxy)-phenyl]-morpholine
2-[4-(2,6-dimethyl-phenylsulfanyl)-phenyl]-morpholine
2-[4-(2,3-dichloro-phenylsulfanyl)-phenyl]-morpholine
2-(4-o-Tolylsulfanyl-phenyl)-morpholine

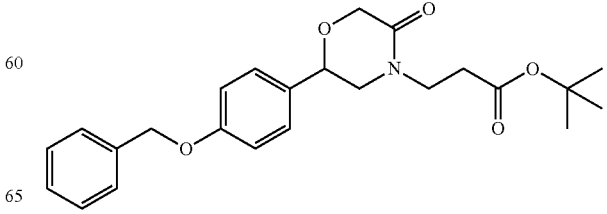

3-[2-(4-Benzyloxy-phenyl)-5-oxo-morpholin-4-yl]-propionic acid tert-butyl ester To a mixture of 6-(4-benzyloxy-phenyl)-morpholin-3-one (13.40 g; 47.3 mmol) and powdered NaOH (3.78 g; 94.6 mmol) in THF (250 mL) was added tert-butyl acrylate (13.7 mL; 94.6 mmol). The resulting mixture was stirred at RT for 2 hours and subsequently concentrated in vacuo. The residue was purified by column chromatography (SiO$_2$, Et$_2$O) to afford 3-[2-(4-benzyloxy-phenyl)-5-oxo-morpholin-4-yl]-propionic acid tert-butyl ester (14.20 g).

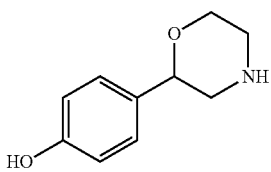

4-Morpholin-2-yl-phenol

To a solution of 4-benzyl-2-(4-benzyloxy-phenyl)-morpholine (8.35 g; 23.2 mmol) in MeOH (100 mL) was added a catalytic amount of palladium hydroxide (0.65 g; ~20 wt % on carbon, wet). The resulting mixture was treated with hydrogen (1 atm.) at RT, overnight. Subsequently, the mixture was filtered over kieselguhr, rinsed with MeOH, and concentrated in vacuo to afford 4-morpholin-2-yl-phenol (4.00 g), which was used as such.

The following compounds were made according to a similar method:
2-(4-Benzenesulfonyl-phenyl)-morpholine
2-[4-(Toluene-2-sulfonyl)-phenyl]-morpholine
2-[4-(2-Chloro-benzenesulfonyl)-phenyl]-morpholine
2-[4-(2,6-Dichloro-benzenesulfonyl)-phenyl]-morpholine
4-Morpholin-2-yl-3-trifluoromethyl-phenol
3-Fluoro-4-morpholin-2-yl-phenol
4-(2-Methyl-morpholin-2-yl)-phenol
3-Morpholin-2-yl-phenol
4-(5,5-Dimethyl-morpholin-2-yl)-phenol   4-(6,6-Dimethyl-morpholin-2-yl)-phenol
3-[2-(4-Hydroxy-phenyl)-5-oxo-morpholin-4-yl]-propionic acid tert-butyl ester

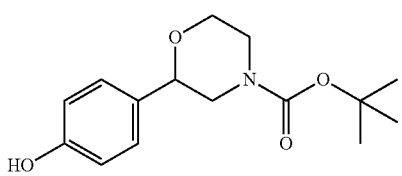

2-(4-Hydroxy-phenyl)-morpholine-4-carboxylic acid tert-butyl ester

A mixture of 4-morpholin-2-yl-phenol (0.99 g; 5.41 mmol) and di-tert-butyl dicarbonate (1.18 g; 5.41 mmol) in CH$_3$CN (50 mL) was stirred at RT for 3 days. Subsequently, the resulting mixture was concentrated in vacuo and the residue was purified by column chromatography (SiO$_2$, CH$_2$Cl$_2$: CH$_3$OH 97:3) to afford 2-(4-hydroxy-phenyl)-morpholine-4-carboxylic acid tert-butyl ester (1.15 g).

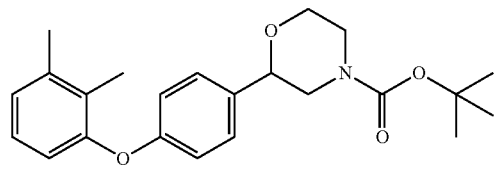 [SMILES: Cc1cccc(Oc2ccc(C3CN(C(=O)OC(C)(C)C)CCO3)cc2)c1C]

2-[4-(2,3-Dimethyl-phenoxy)-phenyl]-morpholine-4-carboxylic acid tert-butyl ester To a degassed solution of 2-(4-hydroxy-phenyl)-morpholine-4-carboxylic acid tert-butyl ester (10.23 g; 36.6 mmol), and 1-iodo-2,3-dimethyl-benzene (10.62 g; 45.8 mmol) in DMSO (50 mL), was added picolinic acid (0.90 g; 7.3 mmol), CuI (0.70 g; 3.7 mmol) and K$_3$PO$_4$ (15.55 g; 73.3 mmol). The resulting mixture was heated overnight, at 90° C. After cooling to RT, brine was added and the mixture extracted with CH$_2$Cl$_2$. The combined organic layers were dried (Na$_2$SO$_4$), filtered and concentrated in vacuo. The residue was purified by column chromatography (SiO$_2$, CH$_2$Cl$_2$) to afford 2-[4-(2,3-dimethyl-phenoxy)-phenyl]-morpholine-4-carboxylic acid tert-butyl ester.

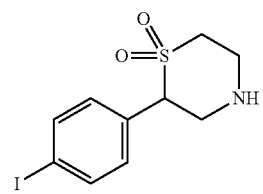 [SMILES: O=S1(=O)CCNCC1c1ccc(I)cc1]

2-(4-Iodo-phenyl)-thiomorpholine 1,1-dioxide

Acetyl chloride (2.8 mL, 39.4 mmol) was added to ethanol (35 mL). The resulting solution was added to 2-(4-Iodophenyl)-1,1-dioxo-1λ$^6$-thiomorpholine-4-carboxylic acid tert-butyl ester (2.16 g; 4.94 mmol), at RT. The resulting mixture was stirred at 55° C. for 2 hours, and subsequently, at RT overnight. The resulting suspension was concentrated in vacuo, and treated with iPr$_2$O. The formed precipitate was collected by filtration and dried in vacuo to afford 2-(4-iodophenyl)-thiomorpholine 1,1-dioxide hydrochloride (1.78 g).

The following compound was made according to a similar method:
2-[4-(2,3-Dimethyl-phenoxy)-phenyl]-morpholine

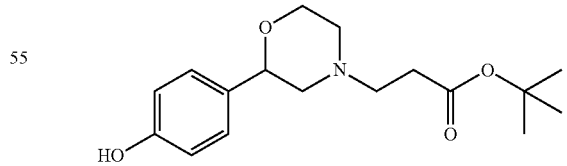

3-[2-(4-Hydroxy-phenyl)-morpholin-4-yl]-propionic acid tert-butyl ester

A mixture of 4-morpholin-2-yl-phenol (3.95 g; 22.0 mmol), and tert-butyl acrylate (9.60 mL; 66.1 mmol) in CH$_3$CN (100 mL) was heated under reflux overnight. After cooling to RT, the mixture was concentrated and purified by column chromatography (SiO$_2$, Et$_2$O) to afford 3-[2-(4-hydroxy-phenyl)-morpholin-4-yl]-propionic acid tert-butyl ester (5.22 g).

The following compounds were made in a similar manner:

3-{2-[4-(2,6-Dichloro-phenylamino)-phenyl]-morpholin-4-yl}-propionic acid tert-butyl ester 3-{2-[4-(2,6-Dimethyl-phenylamino)-phenyl]-morpholin-4-yl}-propionic acid tert-butyl ester 3-{2-[4-(2,6-Dimethyl-benzoyl)-phenyl]-morpholin-4-yl}-propionic acid tert-butyl ester 3-{2-[4-(2,6-Dichloro-benzoyl)-phenyl]-morpholin-4-yl}-propionic acid tert-butyl ester 3-{2-[4-(3-Trifluoromethyl-benzoyl)-phenyl]-morpholin-4-yl}-propionic acid tert-butyl ester 3-{2-[4-(3-Trifluoromethyl-phenoxy)-phenyl]-morpholin-4-yl}-propionic acid tert-butyl ester 3-[2-(4-o-Tolyloxy-phenyl)-morpholin-4-yl]-propionic acid tert-butyl ester 3-{2-[4-(2,6-Dimethyl-phenoxy)-phenyl]-morpholin-4-yl}-propionic acid tert-butyl ester 3-{2-[4-(2-Methyl-benzoyl)-phenyl]-morpholin-4-yl}-propionic acid tert-butyl ester 3-[2-(4-Hydroxy-2-trifluoromethyl-phenyl)-morpholin-4-yl]-propionic acid tert-butyl ester.

3-[2-(2-Fluoro-4-hydroxy-phenyl)-morpholin-4-yl]-propionic acid tert-butyl ester.

3-[2-(3-Hydroxy-phenyl)-morpholin-4-yl]-propionic acid tert-butyl ester

3-[2-(4-Hydroxy-phenyl)-5,5-dimethyl-morpholin-4-yl]-propionic acid tert-butyl ester 3-[6-(4-Hydroxy-phenyl)-2,2-dimethyl-morpholin-4-yl]-propionic acid tert-butyl ester 3-{2-[3-Chloro-4-(2,6-dichloro-phenoxy)-phenyl]-morpholin-4-yl}-propionic acid tert-butyl ester 3-[2-(4-Benzenesulfonyl-phenyl)-morpholin-4-yl]-propionic acid tert-butyl ester.

3-{2-[4-(Toluene-2-sulfonyl)-phenyl]-morpholin-4-yl}-propionic acid tert-butyl ester.

3-{2-[4-(2-Chloro-benzenesulfonyl)-phenyl]-morpholin-4-yl}-propionic acid tert-butyl ester 3-{2-[4-(2,6-Dichloro-benzenesulfonyl)-phenyl]-morpholin-4-yl}-propionic acid tert-butyl ester 3-[2-(4-Hydroxy-phenyl)-2-methyl-morpholin-4-yl]-propionic acid tert-butyl ester 3-[2-(4-Bromo-phenyl)-thiomorpholin-4-yl]-propionic acid tert-butyl ester 3-[2-(4-Iodo-phenyl)-1,1-dioxo-1λ$^6$-thiomorpholin-4-yl]-propionic acid tert-butyl ester 3-{2-[4-(2,6-Dimethyl-phenylsulfanyl)-phenyl]-morpholin-4-yl}-propionic acid tert-butyl ester 3-{2-[4-(2,3-Dichloro-phenylsulfanyl)-phenyl]-morpholin-4-yl}-propionic acid tert-butyl ester 3-[2-(4-o-Tolylsulfanyl-phenyl)-morpholin-4-yl]-propionic acid tert-butyl ester

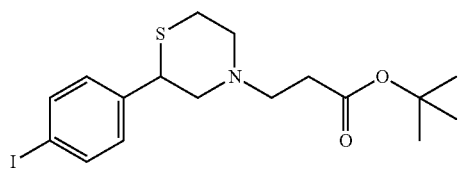 [SMILES: CC(C)(C)OC(=O)CCN1CCSC(c2ccc(I)cc2)C1]

3-[2-(4-Iodo-phenyl)-thiomorpholin-4-yl]-propionic acid tert-butyl ester

To a degassed solution of 3-[2-(4-bromo-phenyl)-thiomorpholin-4-yl]-propionic acid tert-butyl ester (22.15 g; 57.33 mmol) and N,N'-dimethylethylenediamine (3.05 mL; 28.7 mmol) in 1,4-dioxane (250 mL) was added CuI (1.09 g; 5.73 mmol), and NaI (21.48 g; 143.33 mmol). The resulting mixture was heated at 130° C., for 4 days, in sealed flask. After cooling to RT the mixture was concentrated in vacuol and purified by column chromatography (SiO2, Et$_2$O/hexanes 2:3) to afford 3-[2-(4-iodo-phenyl)-thiomorpholin-4-yl]-propionic acid tert-butyl ester (19.30 g).

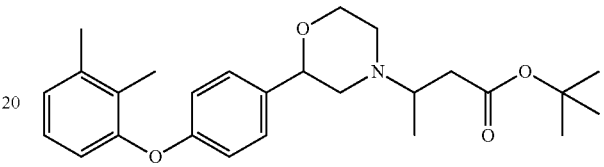

3-{2-[4-(2,3-Dimethyl-phenoxy)-phenyl]-morpholin-4-yl}-butyric acid tert-butyl ester A mixture of 2-[4-(2,3-dimethyl-phenoxy)-phenyl]-morpholine (1.00 g; 3.13 mmol), tert-butyl acetoacetate (2.07 mL; 12.5 mmol), sodium triacetoxyborohydride (1.86 g; 8.75 mmol), and a drop of acetic acid, in 1,2-dichloroethane (20 mL) was stirred overnight, at RT. The resulting mixture was treated with 5% aqueous NaHCO$_3$ and extracted with CH$_2$Cl$_2$. The combined organic layers were dried (Na$_2$SO$_4$), filtered, concentrated in vacuo, and purified by column chromatography (SiO$_2$, Et$_2$O/hexanes 1:3) to afford 3-{2-[4-(2,3-dimethyl-phenoxy)-phenyl]-morpholin-4-yl}-butyric acid tert-butyl ester (1.17 g

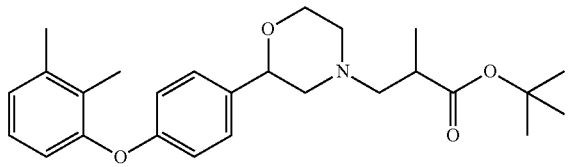 [SMILES: Cc1cccc(Oc2ccc(C3CN(CC(C)C(=O)OC(C)(C)C)CCO3)cc2)c1C]

3-{2-[4-(2,3-Dimethyl-phenoxy)-phenyl]-morpholin-4-yl}-2-methyl-propionic acid tert-butyl ester A mixture of 2-[4-(2,3-dimethyl-phenoxy)-phenyl]-morpholine (0.60 g; 1.9 mmol), tert-butyl methacrylate (0.61 ml; 3.8 mmol), 1,8-diazabicyclo[5.4.0]undec-7-ene (0.84 ml; 5.6 mmol), and DMF (10 mL) was heated at 140° C., overnight, in a closed vessel. After cooling to room temperature, the mixture was partitioned between 5% aqueous NaHCO$_3$ and EtOAc. The organic layer was dried (MgSO$_4$), filtered, and concentrated in vacuo. The residue was purified by column chromatography (SiO$_2$, Et$_2$O/hexanes 1:9) to afford 3-{2-[4-(2,3-dimethyl-phenoxy)-phenyl]-morpholin-4-yl}-2-methyl-propionic acid tert-butyl ester (0.27 g).

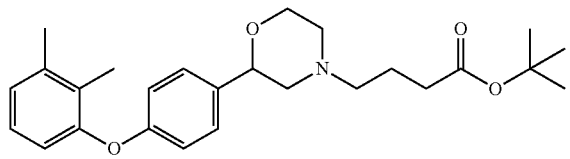 [SMILES: Cc1cccc(Oc2ccc(C3CN(CCCC(=O)OC(C)(C)C)CCO3)cc2)c1C]

4-{2-[4-(2,3-Dimethyl-phenoxy)-phenyl]-morpholin-4-yl}-butyric acid tert-butyl ester A mixture of 2-[4-(2,3-dimethyl-phenoxy)-phenyl]-morpholine (0.40 g; 1.2 mmol), $K_2CO_3$ (0.49 g; 3.6 mmol), KI (0.22 g; 1.31 mmol), 4-bromo-butyric acid tert-butyl ester (0.32 g; 1.43 mmol), and $CH_3CN$ (30 mL), was heated under reflux, overnight. After cooling to RT the mixture was concentrated in vacuo, and the residue was purified by column chromatography ($SiO_2$, $Et_2O$/hexanes 1:1) to afford 4-{2-[4-(2,3-dimethyl-phenoxy)-phenyl]-morpholin-4-yl}-butyric acid tert-butyl ester (0.38 g).

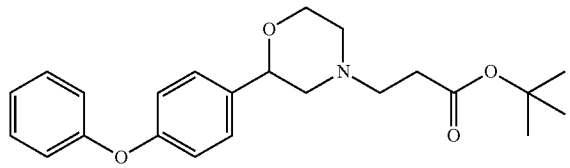 [SMILES: CC(C)(C)OC(=O)CCN1CCOC(c2ccc(Oc3ccccc3)cc2)C1]

3-[2-(4-Phenoxy-phenyl)-morpholin-4-yl]-propionic acid tert-butyl ester

To a mixture of $Cs_2CO_3$ (70 mg; 0.21 mmol), 3-[2-(4-Hydroxy-phenyl)-morpholin-4-yl]-propionic acid tert-butyl ester (33.8 mg, 0.11 mmol) and bromobenzene (12.6 µL, 0.12 mmol) was added 0.5 mL of a freshly prepared catalyst stock solution (see below) in a 2-5 mL Biotage® microwave vial. The vial was briefly flushed with $N_2$ and sealed to maintain a semi-inert atmosphere. The resulting mixture was heated for 22 h, at 140° C. After cooling to room temperature, water (5 mL) was added and the mixture was extracted with EtOAc (1×7.5 mL, 2×5 mL). The combined organic layers were concentrated in vacuo, and the residue was purified by preparative TLC ($SiO_2$, $CH_2Cl_2$/MeOH 99:1) to afford 3-[2-(4-phenoxy-phenyl)-morpholin-4-yl]-propionic acid tert-butyl ester (49 mg). The catalyst stock solution was prepared as follows: To a suspension of copper(I)iodide (73 mg, 0.16 mmol) in anhydrous toluene (9 mL) was added 1-butylimidazole (127 µL; 120 mg; 0.41 mmol). The solution was purged with $N_2$ for 15 min. and vigorously agitated until all the CuI had fully dissolved.

The following compounds were prepared according to a similar method:

3-{2-[4-(3-Trifluoromethoxy-phenoxy)-phenyl]-morpholin-4-yl}-propionic acid tert-butyl ester 3-{2-[4-(3-Fluoro-5-trifluoromethyl-phenoxy)-phenyl]-morpholin-4-yl}-propionic acid tert-butyl ester 3-{2-[4-(4-Morpholin-4-yl-phenoxy)-phenyl]-morpholin-4-yl}-propionic acid tert-butyl ester 3-{2-[4-(3-Chloro-4-methyl-phenoxy)-phenyl]-morpholin-4-yl}-propionic acid tert-butyl ester 3-{2-[4-(2,5-Bis-trifluoromethyl-phenoxy)-phenyl]-morpholin-4-yl}-propionic acid tert-butyl ester 3-{2-[4-(2,4,6-Trifluoro-phenoxy)-phenyl]-morpholin-4-yl}-propionic acid tert-butyl ester 3-{2-[4-(Quinolin-3-yloxy)-phenyl]-morpholin-4-yl}-propionic acid tert-butyl ester 3-{2-[4-(2,3-Difluoro-phenoxy)-phenyl]-morpholin-4-yl}-propionic acid tert-butyl ester 3-{2-[4-(4-Chloro-3-methyl-phenoxy)-phenyl]-morpholin-4-yl}-propionic acid tert-butyl ester 3-{2-[4-(3-Difluoromethoxy-phenoxy)-phenyl]-morpholin-4-yl}-propionic acid tert-butyl ester 3-{2-[4-(3-Dimethylamino-phenoxy)-phenyl]-morpholin-4-yl}-propionic acid tert-butyl ester 3-{2-[4-(1-Oxo-indan-5-yloxy)-phenyl]-morpholin-4-yl}-propionic acid tert-butyl ester 3-{2-[4-(Isoquinolin-5-yloxy)-phenyl]-morpholin-4-yl}-propionic acid tert-butyl ester 3-{2-[4-(4-Chloro-2-methyl-phenoxy)-phenyl]-morpholin-4-yl}-propionic acid tert-butyl ester 3-{2-[4-(4-Butyl-phenoxy)-phenyl]-morpholin-4-yl}-propionic acid tert-butyl ester 3-{2-[4-(4-Chloro-3-trifluoromethyl-phenoxy)-phenyl]-morpholin-4-yl}-propionic acid tert-butyl ester 3-{2-[4-(Pyrimidin-2-yloxy)-phenyl]-morpholin-4-yl}-propionic acid tert-butyl ester 3-{2-[4-(Naphthalen-1-yloxy)-phenyl]-morpholin-4-yl}-propionic acid tert-butyl ester 3-{2-[4-(2-Fluoro-6-trifluoromethyl-phenoxy)-phenyl]-morpholin-4-yl}-propionic acid tert-butyl ester 3-{2-[4-(4-Difluoromethoxy-phenoxy)-phenyl]-morpholin-4-yl}-propionic acid tert-butyl ester 3-{2-[4-(Pyridin-2-yloxy)-phenyl]-morpholin-4-yl}-propionic acid tert-butyl ester 3-{2-[4-(Isoquinolin-4-yloxy)-phenyl]-morpholin-4-yl}-propionic acid tert-butyl ester 3-{4-[4-(2-tert-Butoxycarbonyl-ethyl)-morpholin-2-yl]-phenoxy}-benzoic acid methyl ester 3-{2-[4-(2-Trifluoromethyl-phenoxy)-phenyl]-morpholin-4-yl}-propionic acid tert-butyl ester 3-[2-(4-m-Tolyloxy-phenyl)-morpholin-4-yl]-propionic acid tert-butyl ester 3-{2-[4-(3,5-Dimethyl-phenoxy)-phenyl]-morpholin-4-yl}-propionic acid tert-butyl ester 3-{2-[4-(Pyridin-3-yloxy)-phenyl]-morpholin-4-yl}-propionic acid tert-butyl ester 3-{2-[4-(4-Fluoro-phenoxy)-phenyl]-morpholin-4-yl}-propionic acid tert-butyl ester 3-{2-[4-(2,3-Dimethyl-phenoxy)-phenyl]-morpholin-4-yl}-propionic acid tert-butyl ester 3-{2-[4-(2,4-Difluoro-phenoxy)-phenyl]-morpholin-4-yl}-propionic acid tert-butyl ester 3-{2-[4-(2,4-Dimethyl-phenoxy)-phenyl]-morpholin-4-yl}-propionic acid tert-butyl ester 3-{2-[4-(2-Methoxy-phenoxy)-phenyl]-morpholin-4-yl}-propionic acid tert-butyl ester 3-{2-[4-(3,5-Difluoro-phenoxy)-phenyl]-morpholin-4-yl}-propionic acid tert-butyl ester 3-{2-[4-(1-Oxo-1,3-dihydro-isobenzofuran-5-yloxy)-phenyl]-morpholin-4-yl}-propionic acid tert-butyl ester 3-{2-[4-(4-Methoxy-phenoxy)-phenyl]-morpholin-4-yl}-propionic acid tert-butyl ester 3-{2-[4-(3,4-Dimethyl-phenoxy)-phenyl]-morpholin-4-yl}-propionic acid tert-butyl ester 3-{2-[4-(4-Trifluoromethyl-phenoxy)-phenyl]-morpholin-4-yl}-propionic acid tert-butyl ester 3-{2-[4-(2,5-Dimethyl-phenoxy)-phenyl]-morpholin-4-yl}-propionic acid tert-butyl ester 3-{2-[4-(3-Fluoro-phenoxy)-phenyl]-morpholin-4-yl}-propionic acid tert-butyl ester 3-{2-[4-(3-Methoxy-phenoxy)-phenyl]-morpholin-4-yl}-propionic acid tert-butyl ester 3-{2-[4-(Benzo[1,3]dioxol-5-yloxy)-phenyl]-morpholin-4-yl}-propionic acid tert-butyl ester 3-{2-[4-(3-Fluoro-4-methyl-phenoxy)-phenyl]-morpholin-4-yl}-propionic acid tert-butyl ester 3-{2-[4-(4-Methanesulfonyl-phenoxy)-phenyl]-morpholin-4-yl}-propionic acid tert-butyl ester 3-{2-[4-(4-Acetyl-phenoxy)-phenyl]-morpholin-4-yl}-propionic acid tert-butyl ester 3-{2-[4-(Biphenyl-4-yloxy)-phenyl]-morpholin-4-yl}-propionic acid tert-butyl ester 3-{2-[4-(4-Benzyloxy-phenoxy)-phenyl]-morpholin-4-yl}-propionic acid tert-butyl ester 3-{2-[4-(4-Trifluoromethoxy-phenoxy)-phenyl]-morpholin-4-yl}-propionic acid tert-butyl ester 3-{2-[4-(2-Trifluoromethoxy-phenoxy)-phenyl]-morpholin-4-yl}-propionic acid tert-butyl ester 3-{2-[4-(2-Acetylamino-phenoxy)-phenyl]-morpholin-4-yl}-propionic acid tert-butyl ester 3-{2-[4-(2-Fluoro-phenoxy)-phenyl]-morpholin-4-yl}-propionic acid tert-butyl ester 3-{2-[4-(2,5-Difluoro-phenoxy)-phenyl]-morpholin-4-yl}-propionic acid tert-butyl ester 3-{2-[4-(2,3-Dichloro-phenoxy)-phenyl]-morpholin-4-yl}-propionic acid tert-butyl ester 3-[2-(4-p-Tolyloxy-phenyl)-morpholin-4-yl]-propionic acid tert-butyl ester 3-{2-[4-(3,4-Dichloro-phenoxy)-phenyl]-morpholin-4-yl}-propionic acid tert-butyl ester 3-{2-[4-(3,5-Bis-trifluoromethyl-phenoxy)-phenyl]-morpholin-4-yl}-propionic acid tert-butyl ester 3-{2-[4-(3,5-Dichloro-phenoxy)-phenyl]-morpholin-4-yl}-propionic acid tert-butyl ester 3-{2-[4-(Naphthalen-2-yloxy)-phenyl]-morpholin-4-yl}-propionic acid tert-butyl ester 3-{2-[4-(2,6-Dimethyl-phenoxy)-phenyl]-5-oxo-morpholin-4-yl}-propionic acid tert-butyl ester

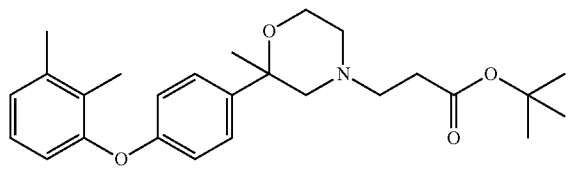 [SMILES: Cc1cccc(Oc2ccc(C3(C)CN(CCC(=O)OC(C)(C)C)CCO3)cc2)c1C]

3-{2-[4-(2,3-Dimethyl-phenoxy)-phenyl]-2-methyl-morpholin-4-yl}-propionic acid tert-butyl ester To a degassed solution of 3-[2-(4-hydroxy-phenyl)-2-methyl-morpholin-4-yl]-propionic acid tert-butyl ester (1.07 g; 3.33 mmol), and 3-iodo-o-xylene (0.97 g; 4.16 mmol) in DMSO (20 mL) was added picolinic acid (82 mg; 0.67 mmol), CuI (63.4 mg; 0.33 mmol) and powdered (1.41 g; 6.66 mmol). The resulting mixture was heated for 24 h, at 90° C. After cooling to room temperature, brine was added and the mixture extracted with CH$_2$Cl$_2$. The combined layers were dried (Na$_2$SO$_4$), filtered, and concentrated in vacuo. The residue was purified by column chromatography (SiO$_2$, Et$_2$O/hexanes 1:1) to afford 3-{2-[4-(2,3-dimethyl-phenoxy)-phenyl]-2-methyl-morpholin-4-yl}-propionic acid tert-butyl ester (1.32 g).

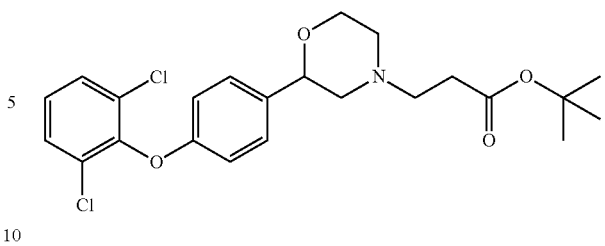

3-{2-[4-(2,6-Dichloro-phenoxy)-phenyl]-morpholin-4-yl}-propionic acid tert-butyl ester A mixture of 3-[2-(4-hydroxy-phenyl)-morpholin-4-yl]-propionic acid tert-butyl ester (200 mg; 0.65 mmol), 2,6-dichlorofluorobenzene (107.35 mg; 0.65 mmol) and K$_2$CO$_3$ (134.9 mg; 0.98 mmol), in DMF (10 mL) was heated at 100° C., for 2 days. After cooling to RT the mixture was diluted with Et$_2$O and washed with water (3 times). The combined organic layers were dried (Na$_2$SO$_4$), filtered, and concentrated in vacuo. The residue was purified by column chromatography (Et$_2$O) to afford 3-{2-[4-(2,6-dichloro-phenoxy)-phenyl]-morpholin-4-yl}-propionic acid tert-butyl ester: (150.00 mg).

The following compounds were prepared according to a similar method:

3-{2-[4-(2,6-Dichloro-phenoxy)-phenyl]-5,5-dimethyl-morpholin-4-yl}-propionic acid tert-butyl ester 3-{6-[4-(2,6-Dichloro-phenoxy)-phenyl]-2,2-dimethyl-morpholin-4-yl}-propionic acid tert-butyl ester 3-{2-[4-(2,6-Dichloro-phenoxy)-2-fluoro-phenyl]-morpholin-4-yl}-propionic acid tert-butyl ester 3-{2-[4-(2,6-Dichloro-phenoxy)-2-trifluoromethyl-phenyl]-morpholin-4-yl}-propionic acid tert-butyl ester 3-{2-[4-(2,6-Dichloro-phenoxy)-phenyl]-2-methyl-morpholin-4-yl}-propionic acid tert-butyl ester

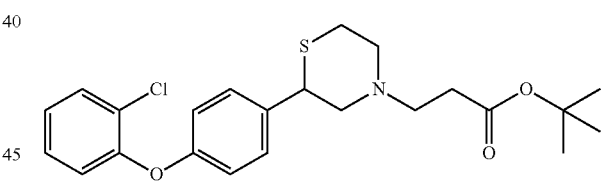

3-{2-[4-(2-Chloro-phenoxy)-phenyl]-thiomorpholin-4-yl}-propionic acid tert-butyl ester To a degassed solution of 3-[2-(4-iodo-phenyl)-thiomorpholin-4-yl]-propionic acid tert-butyl ester (0.40 g; 0.92 mmol), and 2-chlorophenol (0.28 g; 2.22 mmol) in DMSO, was added picolinic acid (22.7 mg; 0.18 mmol), CuI (17.6 mg; 0.09 mmol) and K$_3$PO$_4$ (0.78 g; 3.69 mmol). The resulting mixture was heated overnight, at 90° C. After cooling to RT, water was added and the mixture extracted with CH$_2$Cl$_2$. The organic layer was dried (Na$_2$SO$_4$), filtered and concentrated in vacuo. The residue was purified by column chromatography (SiO$_2$, Et$_2$O/hexanes 1:2) to afford 3-{2-[4-(2-Chloro-phenoxy)-phenyl]-thiomorpholin-4-yl}-propionic acid tert-butyl ester (0.15 g).

The following compounds were prepared according to a similar method:

3-{2-[4-(2,3-Dimethyl-phenoxy)-phenyl]-thiomorpholin-4-yl}-propionic acid tert-butyl ester 3-{2-[4-(2-Chloro-6-methyl-phenoxy)-phenyl]-thiomorpholin-4-yl}-propionic acid tert-butyl ester The following compound was prepared according to a similar method from 3-[2-(4-iodo-phenyl)-1,1-dioxo-1λ$^6$-thiomorpholin-4-yl]-propionic acid tert-butyl ester:

3-{2-[4-(2,3-Dimethyl-phenoxy)-phenyl]-1,1-dioxo-1λ$^6$-thiomorpholin-4-yl}-propionic acid tert-butyl ester

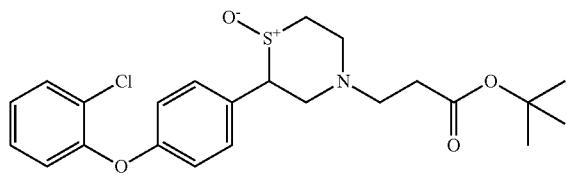 [SMILES: CC(C)(C)OC(=O)CCN1CC[S+]([O-])C(c2ccc(Oc3ccccc3Cl)cc2)C1]

3-{2-[4-(2-Chloro-phenoxy)-phenyl]-1-oxo-thiomorpholin-4-yl}-propionic acid tert-butyl ester To a solution of 3-{2-[4-(2-Chloro-phenoxy)-phenyl]-thiomorpholin-4-yl}-propionic acid tert-butyl ester (0.28 g; 0.65 mmol) in MeOH (10 mL) was added, dropwise, a solution of OXONE® (0.20 g; 0.32 mmol) in water (10 mL), at 0° C. The mixture was stirred for 2 hours at 0° C., and then allowed to warm to room temperature overnight. Subsequently, water, brine, and 25% aqueous NH$_4$OH were added and the mixture extracted with EtOAc. The combined organic layers were dried (Na$_2$SO$_4$), filtered and concentrated in vacuo. The residue was purified by column chromatography (SiO$_2$, CH$_2$Cl$_2$/MeOH 98:2) to afford 3-{2-[4-(2-Chloro-phenoxy)-phenyl]-1-oxo-thiomorpholin-4-yl}-propionic acid tert-butyl ester (0.19 g).

The following compound was made in a similar manner:
3-{2-[4-(2,3-Dimethyl-phenoxy)-phenyl]-1-oxo-thiomorpholin-4-yl}-propionic acid tert-butyl ester §4. Syntheses of Specific Compounds (See Table 1)
Method A:

Compound 1: 3-{2-[4-(2,6-Dichloro-phenylamino)-phenyl]-morpholin-4-yl}-propionic acid hydrochloride 3-{2-[4-(2,6-Dichloro-phenylamino)-phenyl]-morpholin-4-yl}-propionic acid tert-butyl ester (0.36 g; 0.80 mmol) was treated with HCl in 1,4-dioxane (3.99 mL; 4.00 mol/L; 15.95 mmol) and stirred overnight at room temperature. The solvent was removed in vacuo and the residue treated with iPr$_2$O. The formed precipitate was collected by filtration and dried in vacuo, overnight to afford 3-{2-[4-(2,6-Dichloro-phenylamino)-phenyl]-morpholin-4-yl}-propionic acid hydrochloride (0.30 g). $^1$H NMR (400 MHz, DMSO-d$_6$) δ ppm 2.83-2.98 (1H, m) 2.98-3.20 (1H, m) 3.21-3.36 (1H, m) 3.38-3.48 (1H, m) 3.49-3.55 (1H, m) 3.97 (1H, t, J=12.6 Hz) 4.04-4.18 (1H, m) 4.72 (1H, d) 6.53 (1H, d) 7.14 (1H, d) 7.29 (1H, t, J=8.1 Hz) 7.57 (1H, d) 8.03 (1H, s).

The following compounds were made in a similar manner:

Compound 2: 3-{2-[4-(2,6-Dimethyl-phenylamino)-phenyl]-morpholin-4-yl}-propionic acid hydrochloride $^1$H NMR (400 MHz, DMSO-d$_6$) δ ppm 2.12 (s, 6H) 2.85-2.94 (m, 2H) 3.02-3.14 (m, 2H) 3.27-3.35 (m, 2H) 3.40-3.54 (m, 2H) 3.92-4.12 (m, 2H) 4.70 (d, J=11.3 Hz, 1H) 6.40 (d, J=8.8 Hz, 2H) 7.05-7.15 (m, 5H) 7.50 (bs, 1H) 11.8 (bs, 1H) 12.8 (bs, 1H).

Compound 3: 3-{2-[4-(2,6-Dimethyl-benzoyl)-phenyl]-morpholin-4-yl}-propionic acid hydrochloride $^1$H NMR (300 MHz, CD$_3$OD) δ ppm 2.09 (s, 6H), 2.91 (t, J=7 Hz, 2H) 3.13 (t, J=12 Hz, 1H) 3.51 (t, J=7 Hz, 2H) 3.62 (d, J=12 Hz, 1H) 3.76 (d, J=12 Hz, 1H) 4.0-4.1 (m, 1H) 4.32 (dd, J=13 Hz J=3 Hz, 1H) 4.93 (bd, J=12 Hz, 1H) 7.15 (d, J=8 Hz, 2H), 7.30 (dd, J=8 Hz, 1H) 7.61 (d, J=8 Hz, 2H), 7.82 (d, J=8 Hz, 2H).

Compound 4: 3-{2-[4-(3-Trifluoromethyl-benzoyl)-phenyl]-morpholin-4-yl}-propionic acid hydrochloride $^1$H NMR (300 MHz, CD$_3$OD) δ ppm 2.95 (t, J=7 Hz, 2H) 3.19 (t, J=12 Hz, 1H) 3.54 (t, J=7 Hz, 2H) 3.6-3.8 (m, 1H) 3.82 (d, J=13 Hz, 1H) 4.09 (t, J=12 Hz, 1H) 4.3-4.4 (m, 1H) 4.9-5.0 (m, 1H) 7.66 (d, J=8 Hz, 2H), 7.78 (t, J=8 Hz, 1H) 7.86 (d, J=8 Hz, 2H) 7.9-8.1 (m, 3H).

Compound 5: 3-{2-[4-(2-Methyl-benzoyl)-phenyl]-morpholin-4-yl}-propionic acid hydrochloride $^1$H NMR (300 MHz, CD$_3$OD) δ ppm 2.30 (s, 3H) 2.93 (t, J=7 Hz, 2H) 3.16 (dd, J=12 Hz J=12 Hz, 1H) 3.53 (t, J=7 Hz, 2H) 3.64 (d, J=12 Hz, 1H) 3.78 (d, J=12 Hz, 1H) 4.07 (dt, J=13 Hz J=2 Hz, 1H) 4.33 (dd, J=13 Hz J=3 Hz, 1H) 4.95 (dd, J=12 Hz J=2 Hz, 1H) 7.3-7.5 (m, 3H), 7.61 (d, J=8 Hz, 2H), 7.82 (d, J=8 Hz, 2H).

Compound 6: 3-{2-[4-(2,6-Dichloro-benzoyl)-phenyl]-morpholin-4-yl}-propionic acid hydrochloride $^1$H NMR (300 MHz, CD$_3$OD) δ ppm 2.92 (t, J=7 Hz, 2H) 3.14 (t, J=12 Hz, 1H) 3.60-3.68 (m, 2H) 3.76-3.80 (m, 1H) 4.06 (t, J=13 Hz, 1H) 4.33 (dd, J=13 Hz J=3 Hz, 1H) 4.95 (d, J=11 Hz, 1H) 7.53-7.55 (m, 3H), 7.64 (d, J=8 Hz, 2H), 7.85 (d, J=8 Hz, 2H).

Compound 7: 3-[2-(4-o-Tolyloxy-phenyl)-morpholin-4-yl]-propionic acid hydrochloride $^1$H NMR (300 MHz, CD$_3$OD) δ ppm 2.17 (s, 3H) 2.90 (t, J=7 Hz, 2H) 3.14 (t, J=12 Hz, 1H) 3.2-3.3 (m, 1H) 3.49 (t, J=7 Hz, 2H) 3.5-3.7 (m, 2H) 4.01 (t, J=12 Hz, 1H) 4.2-4.3 (m, 1H) 4.7-4.8 (m, 1H) 6.8-6.9 (m, 3H) 7.0-7.4 (m, 5H).

Compound 8: 3-{2-[4-(3-Trifluoromethyl-phenoxy)-phenyl]-morpholin-4-yl}-propionic acid hydrochloride $^1$H NMR (300 MHz, CD$_3$OD) δ ppm 2.90 (t, J=7 Hz, 2H) 3.15 (t, J=12 Hz, 1H) 3.50 (t, J=7 Hz, 2H) 3.59 (d, J=12 Hz, 1H) 3.69 (d, J=13 Hz, 1H) 4.02 (t, J=13 Hz, 1H) 4.28 (dd, J=13 Hz J=3 Hz, 1H) 4.7-4.9 (m, 1H) 7.09 (d, J=8 Hz, 2H), 7.2-7.3 (m, 2H) 7.4-7.6 (m, 4H).

Compound 9: 3-{2-[4-(2,6-Dimethyl-phenoxy)-phenyl]-morpholin-4-yl}-propionic acid hydrochloride $^1$H NMR (300 MHz, CD$_3$OD) δ ppm 2.07 (s, 6H), 2.88 (t, J=7 Hz, 2H) 3.13 (t, J=12 Hz, 1H) 3.2-3.3 (m, 1H) 3.48 (t, J=7 Hz, 2H) 3.58 (d, J=13 Hz, 1H) 3.99 (t, J=12 Hz, 1H) 4.24 (dd, J=13 Hz J=3 Hz, 1H) 4.7-4.8 (m, 1H) 6.75 (d, J=9 Hz, 2H) 7.0-7.2 (m, 3H), 7.34 (d, J=9 Hz, 2H).

Compound 10: 3-{2-[4-(2,6-Dichloro-phenoxy)-phenyl]-morpholin-4-yl}-propionic acid hydrochloride ¹H NMR (400 MHz, DMSO-d₆) δ ppm 2.87 (2H, ddd, J=11.8, 3.7, 3.5 Hz) 3.02-3.18 (2H, m) 3.32 (2H, t, J=8.5 Hz) 3.47 (2H, dd, J=13.3, 1.1 Hz) 3.58-3.67 (1H, m) 3.97 (1H, t, J=12.5 Hz) 4.10-4.19 (1H, m) 4.80 (1H, d, J=11.6 Hz) 6.83-6.89 (2H, m) 7.34-7.43 (3H, m) 7.67 (2H, d, J=8.3 Hz).

Compound 69: 3-{2-[3-Chloro-4-(2,6-dichloro-phenoxy)-phenyl]-morpholin-4-yl}-propionic acid hydrochloride Mp=224-227° C.

Compound 70: 3-{2-[4-(2,6-Dichloro-phenoxy)-2-fluoro-phenyl]-morpholin-4-yl}-propionic acid hydrochloride Mp=207-209° C.

Compound 71: 3-{2-[4-(2,6-Dichloro-phenoxy)-2-trifluoromethyl-phenyl]-morpholin-4-yl}-propionic acid hydrochloride Mp=135-136° C.

Compound 72: 3-{2-[4-(2,6-Dichloro-phenoxy)-phenyl]-5,5-dimethyl-morpholin-4-yl}-propionic acid hydrochloride ¹H NMR (400 MHz, DMSO-d₆) δ ppm 1.41 (s, 6H) 2.90-3.02 (m, 3H) 3.12-3.23 (m, 1H) 3.53-3.63 (m, 2H) 3.77-3.83 (m, 1H) 3.94-4.00 (m, 1H) 4.96 (dd, J=11.3, 2.6 Hz, 1H) 6.85 (d, J=8.8 Hz, 2H) 7.36-7.44 (m, 3H) 7.67 (d, J=8.1 Hz, 2H) 11.2 (bs, 1H) 12.7 (bs, 1H).

Compound 73: 3-{6-[4-(2,6-Dichloro-phenoxy)-phenyl]-2,2-dimethyl-morpholin-4-yl}-propionic acid ¹H NMR (400 MHz, DMSO-d₆) δ ppm 1.26 (s, 3H) 1.49 (s, 3H) 2.83-2.93 (m, 2H) 3.25-3.34 (m, 2H) 3.35-3.55 (m, 4H) 4.92 (d, J=11.0 Hz, 1H) 6.85 (d, J=8.8 Hz, 2H) 7.33-7.42 (m, 3H) 7.67 (d, J=8.1 Hz, 2H) 10.5 (bs, 1H) 12.9 (bs, 1H).

Compound 74: 3-[2-(4-Benzenesulfonyl-phenyl)-morpholin-4-yl]-propionic acid hydrochloride ¹H NMR (400 MHz, DMSO-d₆) δ ppm 2.85-2.92 (m, 2H) 2.95-3.05 (m, 1H) 3.06-3.19 (m, 1H) 3.21-3.38 (m, 2H) 3.45-3.52 (m, 1H) 3.65-3.72 (m, 1H) 3.98-4.08 (m, 1H) 4.18 (d, J=11.0 Hz, 1H) 4.97 (d, J=11.0 Hz, 1H) 7.61-7.73 (m, 5H) 7.93-8.05 (m, 4H) 11.5 (bs, 1H) 12.8 (bs, 1H)

Compound 75: 3-{2-[4-(Toluene-2-sulfonyl)-phenyl]-morpholin-4-yl}-propionic acid hydrochloride ¹H NMR (400 MHz, DMSO-d₆) δ ppm 2.37 (s, 3H) 2.87-2.93 (m, 2H) 2.97-3.07 (m, 1H) 3.08-3.19 (m, 1H) 3.24-3.36 (m, 2H) 3.49 (d, J=11.0 Hz, 1H) 3.71 (d, J=11.0 Hz, 1H) 4.00-4.10 (m, 1H) 4.14-4.22 (m, 1H) 5.01 (d, J=10.7 Hz, 1H) 7.39 (d, J=7.7 Hz, 1H) 7.50-7.58 (m, 1H) 7.59-7.67 (m, 3H) 7.92 (d, J=8.5 Hz, 2H) 8.13 (dd, J=7.7, 1.5 Hz, 1H) 11.8 (bs, 1H) 12.6 (bs, 1H).

Compound 76: 3-{2-[4-(2-Chloro-benzenesulfonyl)-phenyl]-morpholin-4-yl}-propionic acid hydrochloride ¹H NMR (400 MHz, DMSO-d₆) δ ppm 2.85-2.91 (m, 2H) 2.98-3.09 (m, 1H) 3.09-3.19 (m, 1H) 3.22-3.38 (m, 2H) 3.49 (d, J=11.8 Hz, 1H) 3.73 (d, J=11.8 Hz, 1H) 3.98-4.10 (m, 1H) 4.15-4.23 (m, 1H) 5.01 (d, J=11.4 Hz, 1H) 7.63-7.78 (m, 5H) 7.97 (d, J=8.5 Hz, 2H) 8.31 (dd, J=7.8, 1.8 Hz, 1H) 11.6 (bs, 1H) 12.7 (bs, 1H).

Compound 77: 3-{2-[4-(2,6-Dichloro-benzenesulfonyl)-phenyl]-morpholin-4-yl}-propionic acid hydrochloride ¹H NMR (400 MHz, DMSO-d₆) δ ppm 2.82-2.91 (m., 2H) 2.96-3.09 (m, 1H) 3.09-3.19 (m, 1H) 3.39-3.55 (m, 3H) 3.73 (d, J=11.8 Hz, 1H) 3.96-4.08 (m, 1H) 4.15-4.24 (m, 1H) 4.99 (d, J=11.9 Hz, 1H) 7.62-7.73 (m, 5H) 8.03 (d, J=8.3 Hz, 2H) 11.2 (bs, 1H) 12.6 (bs, 1H)

Compound 78: 3-{2-[4-(2,6-Dimethyl-phenoxy)-phenyl]-5-oxo-morpholin-4-yl}-propionic acid ¹H NMR (400 MHz, DMSO-d₆) δ ppm 2.05 (s, 6H) 2.47-2.55 (m, 2H) 3.39-3.62 (m, 4H) 4.20 (s, 2H) 4.77-4.83 (m, 1H) 6.73 (d, J=8.7 Hz, 2H) 7.08-7.20 (m, 3H) 7.33 (d, J=8.7 Hz, 2H) 12.5 (bs, 1H).

Compound 79: 3-{2-[4-(2,6-Dichloro-phenoxy)-phenyl]-2-methyl-morpholin-4-yl}-propionic acid hydrochloride ¹H NMR (400 MHz, DMSO-d₆) δ ppm 2.82-3.74 (m, 11H) 3.95-4.15 (m, 2H) 6.85 (br. s., 2H) 7.36-7.43 (m, 1H) 7.47 (d, J=8.5 Hz, 2H) 7.67 (d, J=8.5 Hz, 2H) 10.88-11.13 (br. s., 1H) 12.58-13.03 (br. s., 1H).

Compound 80: 3-{2-[4-(2,3-Dimethyl-phenoxy)-phenyl]-2-methyl-morpholin-4-yl}-propionic acid hydrochloride ¹H NMR (400 MHz, DMSO-d₆) δ ppm 2.07 (s, 3H) 2.28 (s, 3H) 2.82-3.74 (m, 11H) 3.95-4.15 (m, 2H) 6.73-6.90 (m., 3H) 7.03 (d, J=8.5 Hz, 1H) 7.12 (t, J=8.5 Hz, 1H) 7.45 (d, J=8.5 Hz, 2H) 10.88-11.13 (br. s., 1H) 12.58-13.03 (br. s., 1H).

Compound 81: 3-{2-[4-(2,6-Dimethyl-phenylsulfanyl)-phenyl]-morpholin-4-yl}-propionic acid hydrochloride ¹H NMR (400 MHz, DMSO-d₆) δ ppm 2.35 (s, 6H) 2.85-2.96 (m, 2H) 2.99-3.17 (m, 2H) 3.31 (br. s., 2H) 3.46 (d, J=12.3 Hz, 1H) 3.53-3.63 (m, 1H) 3.94-4.17 (m, 2H) 4.82 (d, J=10.5 Hz, 1H) 6.92 (d, J=8.3 Hz, 2H) 7.23-7.36 (m, 5H) 11.0-12.9 (m, 2H).

Compound 82: 3-{2-[4-(2,3-Dichloro-phenylsulfanyl)-phenyl]-morpholin-4-yl}-propionic acid hydrochloride ¹H NMR (400 MHz, DMSO-d₆) δ ppm 2.82-2.96 (m, 2H) 3.03-3.21 (m, 2H) 3.34 (hr. s., 2H) 3.50 (d, J=11.7 Hz, 1H)

3.70 (d, J=11.7 Hz, 1H) 3.98-4.10 (m, 1H) 4.18 (d, J=11.7 Hz, 1H) 4.94 (d, J=10.5 Hz, 1H) 6.86 (d, J=8.0 Hz, 1H) 7.29 (t, J=8.0 Hz, 1H) 7.46-7.58 (m, 5H) 11.0-12.9 (m, 2H).

Compound 83: 3-[2-(4-o-Tolylsulfanyl-phenyl)-morpholin-4-yl]-propionic acid hydrochloride $^1$H NMR (400 MHz, DMSO-d$_6$) δ ppm 2.32 (s, 3H) 2.85-2.92 (m, 2H) 2.99-3.17 (m, 2H) 3.31 (br. s., 2H) 3.44 (d, J=12.4 Hz, 1H) 3.58-3.68 (m, 1H) 3.94-4.04 (m, 1H) 4.12-4.20 (m, 1H) 4.82 (d, J=10.5 Hz, 1H) 7.18-7.40 (m, 8H) 11.0-12.9 (m, 2H).

Compound 84: 3-{2-[3-(2,6-Dimethyl-phenoxy)-phenyl]-morpholin-4-yl}-propionic acid hydrochloride Mp=219-223° C.

Compound 85: 3-{2-[4-(2,3-Dimethyl-phenoxy)-phenyl]-morpholin-4-yl}-butyric acid hydrochloride Mp=165-170° C.

Compound 86: 3-{2-[4-(2,3-Dimethyl-phenoxy)-phenyl]-morpholin-4-yl}-2-methyl-propionic acid hydrochloride Mp=177-180° C.

Compound 87: 4-{2-[4-(2,3-Dimethyl-phenoxy)-phenyl]-morpholin-4-yl}-butyric acid hydrochloride Mp=225-227° C.

Compound 88: 3-{2-[4-(2-Chloro-phenoxy)-phenyl]-thiomorpholin-4-yl}-propionic acid hydrochloride Mp=155-160° C.

Compound 89: 3-{2-[4-(2,3-Dimethyl-phenoxy)-phenyl]-thiomorpholin-4-yl}-propionic acid hydrochloride Mp=178-183° C.

Compound 90: 3-{2-[4-(2-Chloro-6-methyl-phenoxy)-phenyl]-thiomorpholin-4-yl}-propionic acid hydrochloride Mp=192.5-195° C.

Compound 93: 3-{2-[4-(2,3-Dimethyl-phenoxy)-phenyl]-1,1-dioxo-1λ$^6$-thiomorpholin-4-yl}-propionic acid $^1$H NMR (400 MHz, DMSO-d$_6$) δ ppm 2.07 (s, 3H), 2.29 (s, 3H), 2.41 (t, J=7 Hz, 2H), 2.78-2.91 (m, 3H), 3.05-3.30 (m, 5H), 4.42 (dd, J=12 and 4 Hz, 1H), 6.80 (d, J=8 Hz, 1H), 6.84 (d, J=8 Hz, 2H), 7.06 (d, J=8 Hz, 1H), 7.13 (t, J=8 Hz, 1H), 7.36 (d, J=8 Hz, 2H), 12.00-12.70 (bs, 1H).

Method B:

Compound 11: 3-[2-(4-Phenoxy-phenyl)-morpholin-4-yl]-propionic acid hydrochloride 3-[2-(4-Phenoxy-phenyl)-morpholin-4-yl]-propionic acid tert-butyl ester (49 mg) was treated with HCl in 1,4-dioxane (0.5 mL; 4.0 mol/L, 2 mmol) and shaken overnight at room temperature. Removal of the solvent in vacuo yielded 3-[2-(4-phenoxy-phenyl)-morpholin-4-yl]-propionic acid hydrochloride as an amorphous broken white powder (48 mg). $R_t$=1.60 min.

The following compounds were prepared according to a similar method:

Compound 12: 3-{2-[4-(3-Trifluoromethoxy-phenoxy)-phenyl]-morpholin-4-yl}-propionic acid hydrochloride $R_t$=1.89 min.

Compound 13: 3-{2-[4-(3-Fluoro-5-trifluoromethyl-phenoxy)-phenyl]-morpholin-4-yl}-propionic acid hydrochloride $R_t$=1.76 min.

Compound 14: 3-{2-[4-(4-Morpholin-4-yl-phenoxy)-phenyl]-morpholin-4-yl}-propionic acid hydrochloride $R_t$=1.52 min.

Compound 15: 3-{2-[4-(3-Chloro-4-methyl-phenoxy)-phenyl]-morpholin-4-yl}-propionic acid hydrochloride $R_t$=1.78 min.

Compound 16: 3-{2-[4-(2,5-Bis-trifluoromethyl-phenoxy)-phenyl]-morpholin-4-yl}-propionic acid hydrochloride $R_t$=1.80 min.

Compound 17: 3-{2-[4-(2,4,6-Trifluoro-phenoxy)-phenyl]-morpholin-4-yl}-propionic acid hydrochloride $R_t$=1.66 min.

Compound 18: 3-{2-[4-(Quinolin-3-yloxy)-phenyl]-morpholin-4-yl}-propionic acid hydrochloride $R_t$=1.56 min.

Compound 19: 3-{2-[4-(2,3-Difluoro-phenoxy)-phenyl]-morpholin-4-yl}-propionic acid hydrochloride $R_t$=1.65 min.

Compound 20: 3-{2-[4-(4-Chloro-3-methyl-phenoxy)-phenyl]-morpholin-4-yl}-propionic acid hydrochloride $R_t$=1.76 min.

Compound 21: 3-{2-[4-(3-Difluoromethoxy-phenoxy)-phenyl]-morpholin-4-yl}-propionic acid hydrochloride $R_t$=1.69 min.

Compound 22: 3-{2-[4-(3-Dimethylamino-phenoxy)-phenyl]-morpholin-4-yl}-propionic acid hydrochloride $R_t$=1.56 min.

Compound 23: 3-{2-[4-(1-Oxo-indan-5-yloxy)-phenyl]-morpholin-4-yl}-propionic acid hydrochloride $R_t$=1.49 min.

Compound 24: 3-{2-[4-(Isoquinolin-5-yloxy)-phenyl]-morpholin-4-yl}-propionic acid hydrochloride $R_t$=1.32 min.

Compound 25: 3-{2-[4-(4-Chloro-2-methyl-phenoxy)-phenyl]-morpholin-4-yl}-propionic acid hydrochloride $R_t$=1.76 min.

Compound 26: 3-{2-[4-(4-Butyl-phenoxy)-phenyl]-morpholin-4-yl}-propionic acid hydrochloride $R_t$=1.92 min.

Compound 27: 3-{2-[4-(4-Chloro-3-trifluoromethyl-phenoxy)-phenyl]-morpholin-4-yl}-propionic acid hydrochloride $R_t$=1.81 min.

Compound 28: 3-{2-[4-(Pyrimidin-2-yloxy)-phenyl]-morpholin-4-yl}-propionic acid hydrochloride $R_t$=1.31 min.

Compound 29: 3-{2-[4-(Naphthalen-1-yloxy)-phenyl]-morpholin-4-yl}-propionic acid hydrochloride $R_t$=1.73 min.

Compound 30: 3-{2-[4-(2-Fluoro-6-trifluoromethyl-phenoxy)-phenyl]-morpholin-4-yl}-propionic acid hydrochloride $R_t$=1.70 min.

Compound 31: 3-{2-[4-(4-Difluoromethoxy-phenoxy)-phenyl]-morpholin-4-yl}-propionic acid hydrochloride $R_t$=1.68 min.

Compound 32: 3-{2-[4-(Pyridin-2-yloxy)-phenyl]-morpholin-4-yl}-propionic acid hydrochloride $R_t$=1.41 min.

Compound 33: 3-{2-[4-(Isoquinolin-4-yloxy)-phenyl]-morpholin-4-yl}-propionic acid hydrochloride $R_t$=1.42 min.

Compound 34: 3-{4-[4-(2-Carboxy-ethyl)-morpholin-2-yl]-phenoxy}-benzoic acid methyl ester hydrochloride $R_t$=1.63 min.

Compound 35: 3-{2-[4-(2-Trifluoromethyl-phenoxy)-phenyl]-morpholin-4-yl}-propionic acid hydrochloride $R_t$=1.71 min.

Compound 36: 3-[2-(4-m-Tolyloxy-phenyl)-morpholin-4-yl]-propionic acid hydrochloride $R_t$=1.66 min.

Compound 37: 3-{2-[4-(3,5-Dimethyl-phenoxy)-phenyl]-morpholin-4-yl}-propionic acid hydrochloride $R_t$=1.73 min.

Compound 38: 3-{2-[4-(Pyridin-3-yloxy)-phenyl]-morpholin-4-yl}-propionic acid hydrochloride $R_t$=1.31 min.

Compound 39: 3-{2-[4-(4-Fluoro-phenoxy)-phenyl]-morpholin-4-yl}-propionic acid hydrochloride $R_t$=1.61 min.

Compound 40: 3-{2-[4-(2,3-Dimethyl-phenoxy)-phenyl]-morpholin-4-yl}-propionic acid hydrochloride $R_t$=1.74 min.

Compound 41: 3-{2-[4-(2,4-Difluoro-phenoxy)-phenyl]-morpholin-4-yl}-propionic acid hydrochloride $R_t$=1.64 min.

Compound 42: 3-{2-[4-(2,4-Dimethyl-phenoxy)-phenyl]-morpholin-4-yl}-propionic acid hydrochloride $R_t$=1.74 min.

Compound 43: 3-{2-[4-(2-Methoxy-phenoxy)-phenyl]-morpholin-4-yl}-propionic acid hydrochloride $R_t$=1.57 min.

Compound 44: 3-{2-[4-(3,5-Difluoro-phenoxy)-phenyl]-morpholin-4-yl}-propionic acid hydrochloride $R_t$=1.66 min.

Compound 45: 3-{2-[4-(1-Oxo-1,3-dihydro-isobenzofuran-5-yloxy)-phenyl]-morpholin-4-yl}-propionic acid hydrochloride $R_t$=1.47 min.

Compound 46: 3-{2-[4-(4-Methoxy-phenoxy)-phenyl]-morpholin-4-yl}-propionic acid hydrochloride $R_t$=1.59 min.

Compound 47: 3-{2-[4-(3,4-Dimethyl-phenoxy)-phenyl]-morpholin-4-yl}-propionic acid hydrochloride $R_t$=1.74 min.

Compound 48: 3-{2-[4-(4-Trifluoromethyl-phenoxy)-phenyl]-morpholin-4-yl}-propionic acid hydrochloride $R_t$=1.77 min.

Compound 49: 3-{2-[4-(2,5-Dimethyl-phenoxy)-phenyl]-morpholin-4-yl}-propionic acid hydrochloride $R_t$=1.73 min.

Compound 50: 3-{2-[4-(3-Fluoro-phenoxy)-phenyl]-morpholin-4-yl}-propionic acid hydrochloride $R_t$=1.63 min.

Compound 51: 3-{2-[4-(3-Methoxy-phenoxy)-phenyl]-morpholin-4-yl}-propionic acid hydrochloride $R_t$=1.60 min.

Compound 52: 3-{2-[4-(Benzo[1,3]dioxol-5-yloxy)-phenyl]-morpholin-4-yl}-propionic acid hydrochloride $R_t$=1.62 min.

Compound 53: 3-{2-[4-(3-Fluoro-4-methyl-phenoxy)-phenyl]-morpholin-4-yl}-propionic acid hydrochloride $R_t$=1.91 min.

Compound 54: 3-{2-[4-(4-Methanesulfonyl-phenoxy)-phenyl]-morpholin-4-yl}-propionic acid hydrochloride $R_t$=1.46 min.

Compound 55: 3-{2-[4-(4-Acetyl-phenoxy)-phenyl]-morpholin-4-yl}-propionic acid hydrochloride $R_t$=1.54 min.

Compound 56: 3-{2-[4-(Biphenyl-4-yloxy)-phenyl]-morpholin-4-yl}-propionic acid hydrochloride $R_t$=1.00 min.

Compound 57: 3-{2-[4-(4-Benzyloxy-phenoxy)-phenyl]-morpholin-4-yl}-propionic acid hydrochloride $R_t$=1.00 min.

Compound 58: 3-{2-[4-(4-Trifluoromethoxy-phenoxy)-phenyl]-morpholin-4-yl}-propionic acid hydrochloride $R_t$=1.78 min.

Compound 59: 3-{2-[4-(2-Trifluoromethoxy-phenoxy)-phenyl]-morpholin-4-yl}-propionic acid hydrochloride $R_t$=1.73 min.

Compound 60: 3-{2-[4-(2-Acetylamino-phenoxy)-phenyl]-morpholin-4-yl}-propionic acid hydrochloride $R_t$=1.45 min.

Compound 61: 3-{2-[4-(2-Fluoro-phenoxy)-phenyl]-morpholin-4-yl}-propionic acid hydrochloride $R_t$=1.63 min.

Compound 62: 3-{2-[4-(2,5-Difluoro-phenoxy)-phenyl]-morpholin-4-yl}-propionic acid hydrochloride $R_t$=1.63 min.

Compound 63: 3-{2-[4-(2,3-Dichloro-phenoxy)-phenyl]-morpholin-4-yl}-propionic acid hydrochloride $R_t$=1.79 min.

Compound 64: 3-[2-(4-p-Tolyloxy-phenyl)-morpholin-4-yl]-propionic acid hydrochloride $R_t$=1.66 min.

Compound 65: 3-{2-[4-(3,4-Dichloro-phenoxy)-phenyl]-morpholin-4-yl}-propionic acid hydrochloride $R_t$=1.77 min.

Compound 66: 3-{2-[4-(3,5-Bis-trifluoromethyl-phenoxy)-phenyl]-morpholin-4-yl}-propionic acid hydrochloride $R_t$=1.96 min.

Compound 67: 3-{2-[4-(3,5-Dichloro-phenoxy)-phenyl]-morpholin-4-yl}-propionic acid hydrochloride $R_t$=1.82 min.

Compound 68: 3-{2-[4-(Naphthalen-2-yloxy)-phenyl]-morpholin-4-yl}-propionic acid hydrochloride $R_t$=1.75 min.
Method C:

Compound 91: 3-{2-[4-(2-Chloro-phenoxy)-phenyl]-1-oxo-thiomorpholin-4-yl}-propionic acid trifluoroacetic acid salt To a solution of 3-{2-[4-(2-Chloro-phenoxy)-phenyl]-1-oxo-thiomorpholin-4-yl}-propionic acid tert-butyl ester (0.19 g; 0.42 mmol) in CH$_2$Cl$_2$ (10 mL) was added TFA (2 mL). The resulting mixture was stirred, at RT, overnight, treated with toluene, and concentrated in vacuo. The residue was dissolved in CH$_2$Cl$_2$ and concentrated in vacuo to afford 3-{2-[4-(2-Chloro-phenoxy)-phenyl]-1-oxo-thiomorpholin-4-yl}-propionic acid trifluoroacetic acid salt as an oil (0.17 g). $^1$H NMR (400 MHz, DMSO-d$_6$) δ ppm 2.83 (t, J=8 Hz, 2H), 2.92-3.13 (m, 1H), 3.21-3.34 (m, 2H), 3.34-3.44 (m, 2H), 3.44-3.61 (m, 2H), 3.86 (t, J=12 Hz, 1H), 4.44 (d, J=12 Hz, 1H), 7.04 (m, 2H), 7.23 (d, J=8 Hz, 1H), 7.33 (m, 1H), 7.40 (dd, J=8 and 2 Hz, 1H), 7.47 (m, 2H), 7.69 (dd, J=8 and 2 Hz, 1H), 11.00-13.00 (bs, 1H).

The following compound was prepared according to a similar method:

Compound 92: 3-{2-[4-(2,3-Dimethyl-phenoxy)-phenyl]-1-oxo-thiomorpholin-4-yl}-propionic acid trifluoroacetic acid salt $^1$H-NMR (400 Mhz, DMSO-d$_6$) δ ppm 1.97 (s, 3H), 2.20 (s, 3H), 2.75 (t, J=8 Hz, 2H), 3.10-3.28 (m, 2H), 3.28-3.43 (m, 2H), 3.43-3.63 (m, 2H), 3.83 (t, J=12 Hz, 1H), 4.33 (d, J=12 Hz, 1H), 6.72 (d, J=8 Hz, 1H), 6.80 (d, J=8 Hz, 2H), 6.98 (d, J=8 Hz, 2H), 7.06 (t, J=8 Hz, 1H), 7.20 (d, J=8 Hz, 2H), 10.00-12.50 (bs, 1H).

TABLE 1

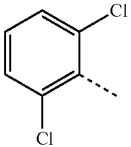

| Comp. | R1 | A | R2 | R5 | Method |
|---|---|---|---|---|---|
| 1 | 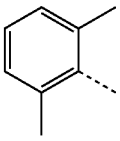 | NH | H | H | A |
| 2 | 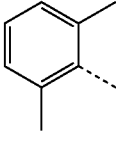 | NH | H | H | A |
| 3 | 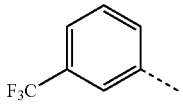 | C=O | H | H | A |
| 4 | 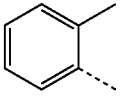 | C=O | H | H | A |
| 5 | 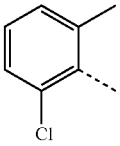 | C=O | H | H | A |
| 6 | 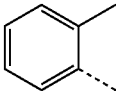 | C=O | H | H | A |
| 7 |  | O | H | H | A |

TABLE 1-continued
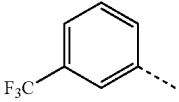
| Comp. | R1 | A | R2 | R5 | Method |
|---|---|---|---|---|---|
| 8 | 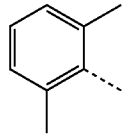 | O | H | H | A |
| 9 | 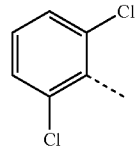 | O | H | H | A |
| 10 | 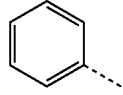 | O | H | H | A |
| 11 | 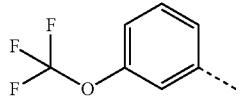 | O | H | H | B |
| 12 | 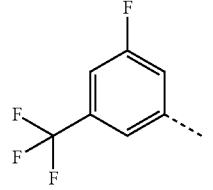 | O | H | H | B |
| 13 | 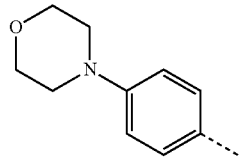 | O | H | H | B |
| 14 | 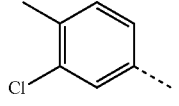 | O | H | H | B |
| 15 | 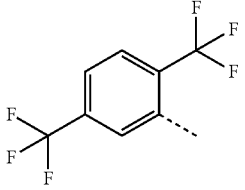 | O | H | H | B |
| 16 |  | O | H | H | B |

TABLE 1-continued

| Comp. | R1 | A | R2 | R5 | Method |
|---|---|---|---|---|---|
| 17 | 2,3,5-trifluorophenyl | O | H | H | B |
| 18 | quinolin-3-yl | O | H | H | B |
| 19 | 2,3-difluorophenyl | O | H | H | B |
| 20 | 4-chloro-3-methylphenyl | O | H | H | B |
| 21 | 3-(difluoromethoxy)phenyl | O | H | H | B |
| 22 | 3-(dimethylamino)phenyl | O | H | H | B |
| 23 | 1-oxo-2,3-dihydro-1H-inden-5-yl | O | H | H | B |
| 24 | isoquinolin-5-yl | O | H | H | B |
| 25 | 4-chloro-2-methylphenyl | O | H | H | B |
| 26 | 4-butylphenyl | O | H | H | B |

TABLE 1-continued
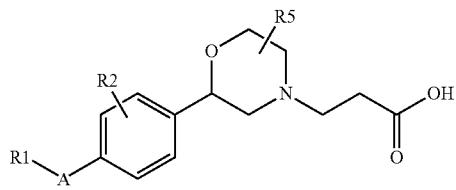
| Comp. | R1 | A | R2 | R5 | Method |
|---|---|---|---|---|---|
| 27 | 2-Cl, 5-CF3-phenyl | O | H | H | B |
| 28 | pyrimidin-2-yl | O | H | H | B |
| 29 | naphthalen-1-yl | O | H | H | B |
| 30 | 2,3-difluoro-CF3-phenyl | O | H | H | B |
| 31 | 4-(OCHF2)-phenyl | O | H | H | B |
| 32 | pyridin-2-yl | O | H | H | B |
| 33 | isoquinolin-4-yl | O | H | H | B |
| 34 | 3-(CO2Me)-phenyl | O | H | H | B |
| 35 | 2-CF3-phenyl | O | H | H | B |

TABLE 1-continued
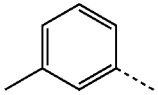
| Comp. | R1 | A | R2 | R5 | Method |
|---|---|---|---|---|---|
| 36 | 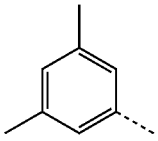 | O | H | H | B |
| 37 | 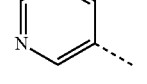 | O | H | H | B |
| 38 | 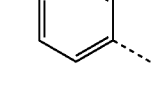 | O | H | H | B |
| 39 | 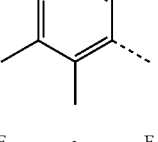 | O | H | H | B |
| 40 | 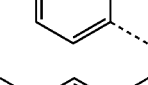 | O | H | H | B |
| 41 | 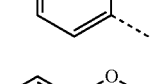 | O | H | H | B |
| 42 | 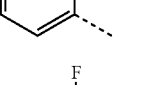 | O | H | H | B |
| 43 | 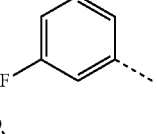 | O | H | H | B |
| 44 | 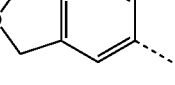 | O | H | H | B |
| 45 | 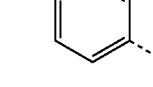 | O | H | H | B |
| 46 |  | O | H | H | B |

TABLE 1-continued

| Comp. | R1 | A | R2 | R5 | Method |
|---|---|---|---|---|---|
| 47 | 3,4-dimethylphenyl | O | H | H | B |
| 48 | 4-(trifluoromethyl)phenyl | O | H | H | B |
| 49 | 2,4-dimethylphenyl | O | H | H | B |
| 50 | 3-fluorophenyl | O | H | H | B |
| 51 | 3-methoxyphenyl | O | H | H | B |
| 52 | benzo[1,3]dioxol-5-yl | O | H | H | B |
| 53 | 3-fluoro-4-methylphenyl | O | H | H | B |
| 54 | 4-(methylsulfonyl)phenyl | O | H | H | B |
| 55 | 4-acetylphenyl | O | H | H | B |
| 56 | biphenyl-4-yl | O | H | H | B |

TABLE 1-continued
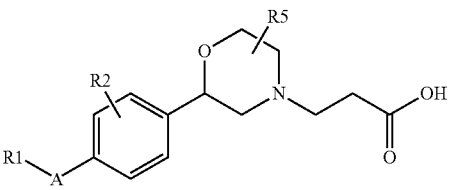
| Comp. | R1 | A | R2 | R5 | Method |
|---|---|---|---|---|---|
| 57 | 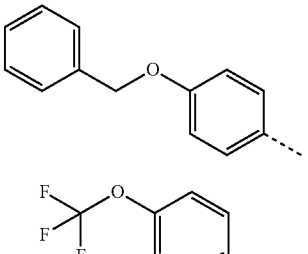 | O | H | H | B |
| 58 | 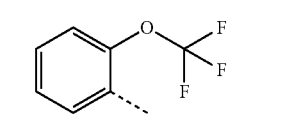 | O | H | H | B |
| 59 | 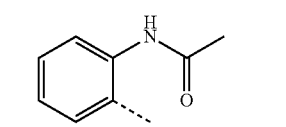 | O | H | H | B |
| 60 | 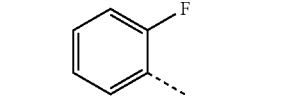 | O | H | H | B |
| 61 | 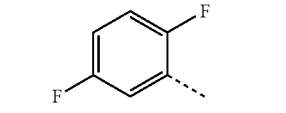 | O | H | H | B |
| 62 | 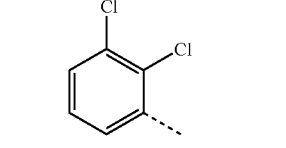 | O | H | H | B |
| 63 | 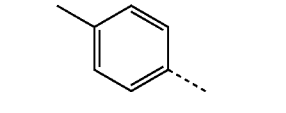 | O | H | H | B |
| 64 | 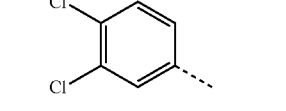 | O | H | H | B |
| 65 | 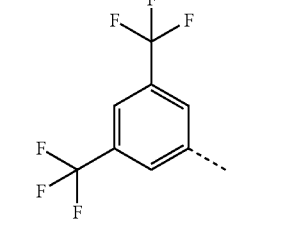 | O | H | H | B |
| 66 | | O | H | H | B |

TABLE 1-continued
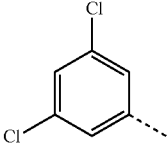
| Comp. | R1 | A | R2 | R5 | Method |
|---|---|---|---|---|---|
| 67 | 3,5-dichlorophenyl | O | H | H | B |
| 68 | 2-naphthyl | O | H | H | B |
| 69 | 2,6-dichlorophenyl | O | 3-Cl | H | A |
| 70 | 2,6-dichlorophenyl | O | 2-F | H | A |
| 71 | 2,6-dichlorophenyl | O | 2-$CF_3$ | H | A |
| 72 | 2,6-dichlorophenyl | O | H | 5,5-$Me_2$ | A |
| 73 | 2,6-dichlorophenyl | O | H | 2,2-$Me_2$ | A |
| 74 | phenyl | $SO_2$ | H | H | A |
| 75 | 2-methylphenyl | $SO_2$ | H | H | A |

TABLE 1-continued
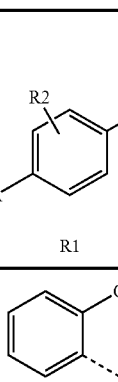
| Comp. | R1 | A | R2 | R5 | Method |
|---|---|---|---|---|---|
| 76 | 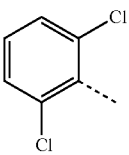 2-Cl-phenyl | SO₂ | H | H | A |
| 77 | 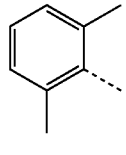 2,6-diCl-phenyl | SO₂ | H | H | A |
| 78 | 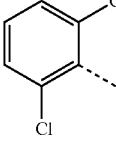 2,3-diMe-phenyl | O | H | 5-oxo | A |
| 79 | 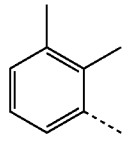 2,6-diCl-phenyl | O | H | 2-Me | A |
| 80 | 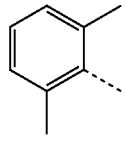 2,3-diMe-phenyl | O | H | 2-Me | A |
| 81 | 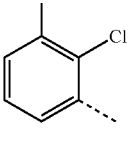 2,3-diMe-phenyl | S | H | H | A |
| 82 | 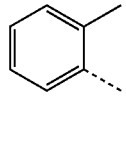 2,3-diCl-phenyl | S | H | H | A |
| 83 | 2-Me-phenyl | S | H | H | A |
| 84 | 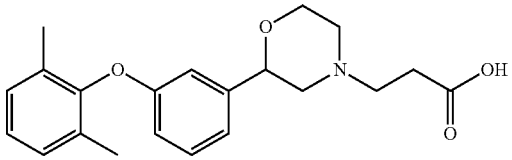 | | | | A |

TABLE 2

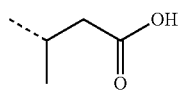

| Comp. | R3 | Method |
|---|---|---|
| 85 | 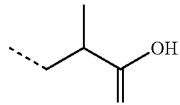 | A |
| 86 | 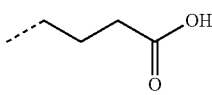 | A |
| 87 | 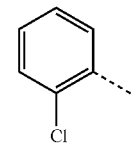 | A |

TABLE 3

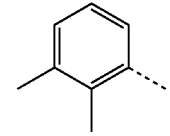

| Comp. | R1 | W | Method |
|---|---|---|---|
| 88 | 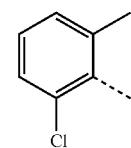 | S | A |
| 89 | 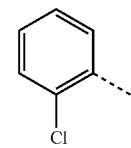 | S | A |
| 90 | 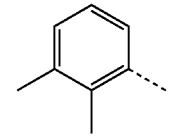 | S | A |
| 91 | | SO | C |
| 92 | | SO | C |

TABLE 3-continued

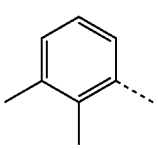

| Comp. | R1 | W | Method |
|---|---|---|---|
| 93 | | $SO_2$ | A |

§5. Pharmacological Tests & Data

In Vitro Functional Activity (Agonism) on Human S1P5 Receptors

The CHO-human-S1P5-Aecorin assay was bought from Euroscreen, Brussels (Euroscreen, Technical dossier, Human Lysophospholid S1P5 (Edg8) receptor, DNA clone and CHO AequoScreen™ recombinant cell-line, catalog no: ES-593-A, September 2006). Human-S1P5-Aequorin cells express mitochondrial targeted apo-Aequorin. Cells have to be loaded with coelanterazine, in order to reconstitute active Aequorin. After binding of agonists to the human S1P5 receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\lambda_{max}$ 469 nm). This luminescent response is dependent on the agonist concentration. Luminescence is measured using the MicroBeta Jet (Perkin Elmer). Agonistic effects of compounds are expressed as $pEC_{50}$. Compounds were tested at a 10 points half log concentration range, and 3 independent experiments were performed in single point's measurements.

In Vitro Functional Activity (Agonism) on Human S1P3 Receptors

The CHO-human-S1P3-Aeqorin assay (CHO/Gα16/AEQ/h-S1P3) was established at Solvay Pharmaceuticals. The plasmid DNA coding for the S1P3 receptor (accession number in GenBank NM_005226 was purchased from UMR cDNA resource Centre (Rolla, Mo.). The pcDNA3.1/hS1P3 construct carrying the mitochondrially targeted apo-Aeqorin and Gα16 protein was transfected in CHO K1 cell-line.

Human-S1P3-Aequorin cells express mitochondrial targeted apo-Aequorin. Cells have to be loaded with coelanterazine, in order to reconstitute active Aequorin. After binding of agonists to the human S1P3 receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\lambda_{max}$ 469 nm). This luminescent response is dependent on the agonist concentration. Luminescence is measured using the MicroBeta Jet (Perkin Elmer). Agonistic effects of compounds are expressed as $pEC_{50}$. Compounds were tested at a 10 points half log concentration range, and 3 independent experiments were performed in single point's measurements.

In Vitro Functional Activity (Agonism) on Human S1P1 Receptors

The CHO-K1-Human S1P1-c-AMP assay was performed at Euroscreenfast, Brussels (Euroscreen, Human S1P1 coupling Gm (Edg1) receptor, catalog no: FAST-0197C, December 2009).

Recombinant CHO-K1 cells expressing human S1P1, grown to mid-log Phase in culture media without antibiotics, detached, centrifuged and re-suspended. For agonist testing cells are mixed with compound and Forskolin and incubated at room temperature. Cells are lyses and cAMP concentration are estimated, according to the manufacturer specification, With the HTRF kit from CIS-BIO International (cat n° 62AM2PEB).

Agonistic effects of compounds are expressed as a percentage of the activity of the reference compound at its $EC_{100}$ concentration, $EC_{50}$ is calculated and results are reported as $pEC_{50}$. Compounds were tested at a 10 points half log concentration range duplicated in 1 experiment.

Pharmacological Data (Receptor Agonism) for Selected Compounds:

| Compound | S1P5 $pEC_{50}$ | S1P1 $pEC_{50}$ | S1P3 $pEC_{50}$ |
|---|---|---|---|
| 2 | 6.2 | nd | <5.0 |
| 6 | 6.3 | <5.5 | <5.0 |
| 15 | 6.3 | nd | <5.0 |
| 26 | 5.7 | nd | 5.3 |
| 29 | 7.2 | nd | <5.0 |
| 35 | 6.7 | nd | <5.0 |
| 47 | 6.7 | nd | <5.0 |
| 57 | 5.7 | nd | <5.0 |
| 64 | 5.8 | nd | <5.0 |
| 68 | 6.2 | nd | <5.0 |
| 73 | 6.8 | <5.5 | nd |
| 80 | 6.2 | <4.5 | <5.0 |
| 87 | 6.0 | nd | nd | nd = not determined.

In Vivo Therapeutic Model; T-Maze

Age-related memory deficits occur in humans and rodents. Spontaneous alternation is the innate tendency of rodents to alternate free choices in a T-maze over a series of successive runs. This sequential procedure relies on working memory and is sensitive to various pharmacological manipulations affecting memory processes (*Aging and the physiology of spatial memory*. Barnes C. A. *Neurobiol. Aging* 1988:563-8; Dember W N, Fowler H. *Spontaneous alternation behavior. Psychol. Bull.* 1958, 55(6):412-427; Gerlai R. *A new continuous alternation task in T-maze detects hippocampal dysfunction in mice. A strain comparison and lesion study. Behav Brain Res* 1998 95(1):91-101).

For this study, male C57BL/6J mice of 2 months or 12 months old may be used in the spontaneous alternation task in the T-maze. In short, mice are subjected to 1 session containing 15 trials, consisting of 1 "forced-choice" trial, followed by 14 "free-choice" trials. The animal is considered as entering one of the arms of the maze when all four paws are placed within this arm. A session is terminated and the animal is removed from the maze as soon as 14 free-choice trials have been performed or 15 min have elapsed, whatever event occurs first. The percentage of alternation over the 14 free-choice trials is determined for each mouse and is used as an index of working memory performance. A compound of the invention may be administrated p.o. for 21 days prior to the T-maze assay and on the day of the T-maze at t=−30 min. Compounds of the invention at doses ranging from of 0.01-15 mg/kg/day may reverse the age-related cognitive decline in the 12-month old C57BL6J mice with up to 100%. Thus, treated 12 month old mice may become identical in their performance as 2 months old vehicle-treated mice.

The invention claimed is:
1. A compound of the formula (I)

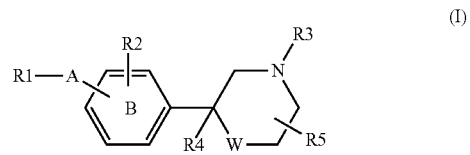

or a pharmaceutically acceptable salt, solvate, or hydrate thereof,
wherein
R1 is selected from:
an aryl substituent selected from the group consisting of a phenyl group, a pyridyl group, a pyrimidinyl group, a biphenyl group, and a naphthyl group, wherein each group is optionally substituted with at least one substituent independently selected from the group consisting of a halogen atom, a (1-6C)alkyl group optionally substituted with at least one fluoro atom, a (1-4C)alkoxy group optionally substituted with at least one fluoro atom, an amino group, a di(1-4C) alkylamino group, a —SO$_2$-(1-4C)alkyl group, a —CO-(1-4C)alkyl group, a —CO—O-(1-4C)alkyl group, and an —NH—CO-(1-4C)alkyl group, or
each group is optionally substituted with a substituent selected from the group consisting of a phenoxy, a benzyl, a benzyloxy, a phenylethyl, and a morpholinyl,
wherein each substituent is optionally substituted with a (1-4C)alkyl group;
an (8-10C)bicyclic group optionally substituted with a (1-4C)alkyl group optionally substituted with at least one fluoro atom or an oxo group; and
a bicyclic heterocycle, optionally substituted with a (1-4C) alkyl group optionally substituted with at least one fluoro atom or an oxo group;
A is selected from the group consisting of —CO—, —NH—, —O—, —S—, —SO—, and —SO$_2$—;
ring structure B optionally contains one nitrogen atom;
R2 is selected from the group consisting of H, a (1-4C) alkyl group optionally substituted with at least one fluoro atom, a (1-4C) alkoxy group optionally substituted with at least one fluoro atom, and a halogen atom;
R3 is selected from the group consisting of a (1-4C)alkylene-R6 group wherein the alkylene group may be substituted with (CH$_2$)$_2$ to form a cyclopropyl moiety or with at least one halogen atom, a (3-6C)cycloalkylene-R6 group, and a —CO—CH$_2$—R6 group, wherein R6 is selected from the group consisting of —OH—, —PO$_3$H$_2$, —COOH, —COO(1-4C)alkyl, and tetrazol-5-yl;
R4 is selected from the group consisting of H and a (1-4C) alkyl group;
R5 is at least one substituent wherein each substituent is independently selected from the group consisting of H, a (1-4C)alkyl group, and an oxo group; and
W is selected from the group consisting of —S—, —SO—, and —SO$_2$—.

2. The compound of claim 1, having the formula (II)

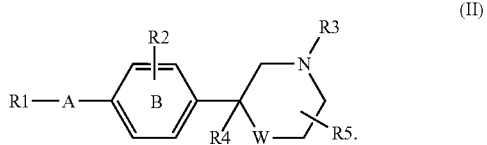

(II)

3. The compound of claim 1, wherein R3 is selected from the group consisting of —(CH$_2$)$_2$—OH, —CH$_2$—COOH, —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH, —CH$_2$—CF$_2$—COOH, —CO—CH$_2$—COOH, —(CH$_2$)$_2$—PO$_3$H$_2$, —(CH$_2$)$_2$—PO$_3$H$_2$, —(CH$_2$)$_3$OPO$_3$H$_2$, —(CH$_2$)$_3$—OPO$_3$H$_2$, —CH$_2$-tetrazol-5-yl, —(CH$_2$)$_2$-tetrazol-5-yl, and —(CH$_2$)$_3$-tetrazol-5-yl; and R4 is H.

4. The compound of claim 2, wherein R3 is —(CH$_2$)$_2$—COOH.

5. The compound of claim 1, wherein R2 is selected from the group consisting of H and halogen.

6. The compound of claim 1, wherein the ring structure B is phenylene.

7. The compound of claim 1, wherein R5 is H.

8. The compound of claim 1, wherein R1 is selected from the group consisting of pyridyl, pyrimidinyl, biphenyl, naphthyl, dihydrobenzofuranyl optionally substituted with oxo, benzdioxanyl, quinolinyl, isoquinolinyl, and phenyl wherein
each is optionally substituted with at least one substituent independently selected from the group consisting of halogen, a (1-6C)alkyl group, a di(1-4C)alkylamino group, a —SO$_2$-(1-4C)alkyl group, a —CO-(1-4C)alkyl group, a —CO—O-(1-4C)alkyl group, a —NH—CO-(1-4C)alkyl group, a difluoromethyl group, a trifluoromethyl group, a difluoromethoxy group, and a trifluoromethoxy group, or each is optionally substituted with a substituent selected from the group consisting of phenoxy, benzyl, benzyloxy, phenylethyl, and morpholinyl.

9. The compound of claim 1, wherein A is selected from the group consisting of —CO—, —NH—, and —O—.

10. The compound of claim 1, wherein the compound is selected from the group consisting of:
3-{2-[4-(2-Chloro-phenoxy)-phenyl]-thiomorpholin-4-yl}-propionic acid,
3-{2-[4-(2,3-Dimethyl-phenoxy)-phenyl]-thiomorpholin-4-yl}-propionic acid,
3-{2-[4-(2-Chloro-6-methyl-phenoxy)-phenyl]-thiomorpholin-4-yl}-propionic acid,
3-{2-[4-(2-Chloro-phenoxy)-phenyl]-1-oxo-thiomorpholin-4-yl}-propionic acid,
3-{2-[4-(2,3-Dimethyl-phenoxy)-phenyl]-1-oxo-thiomorpholin-4-yl}-propionic acid, and
3-{2-[4-(2,3-Dimethyl-phenoxy)-phenyl]-1,1-dioxo-1$\lambda^6$-thiomorpholin-4-yl}-propionic acid,
or a pharmaceutically acceptable salt, solvate, or hydrate of any of the foregoing.

11. A method of treating or alleviating a (vascular) dementia, Nieman's Pick disease, cognitive deficits in schizophrenia, obsessive-compulsive behavior, major depression, multiple sclerosis, or pain, the method comprising administering to a patient in need thereof a compound according to claim 1, or a pharmaceutically acceptable salt, solvate, or hydrate thereof.

12. A pharmaceutical composition comprising the compound of claim 1 and at least one pharmaceutically acceptable auxiliary.

13. A method of treating or alleviating a (vascular) dementia, Nieman's Pick disease, cognitive deficits in schizophrenia, obsessive-compulsive behavior, major depression, multiple sclerosis, or pain, the method comprising administering to a patient in need thereof the pharmaceutical composition according to claim 12.

* * * * *